`US010603337B1`

(12) United States Patent
Ganga, Sr.

(10) Patent No.: US 10,603,337 B1
(45) Date of Patent: *Mar. 31, 2020

(54) ANTIMICROBIAL SKIN CREAM

(71) Applicant: Yvon Samba Ganga, Sr., San Diego, CA (US)

(72) Inventor: Yvon Samba Ganga, Sr., San Diego, CA (US)

( * ) Notice: Subject to any disclaimer, the term of this patent is extended or adjusted under 35 U.S.C. 154(b) by 154 days.

This patent is subject to a terminal disclaimer.

(21) Appl. No.: 15/957,179

(22) Filed: Apr. 19, 2018

Related U.S. Application Data

(63) Continuation of application No. 15/614,967, filed on Jun. 6, 2017, now Pat. No. 10,238,686, and a continuation-in-part of application No. 15/133,172, filed on Apr. 19, 2016, now Pat. No. 9,987,305, and a continuation-in-part of application No. 15/363,940, filed on Nov. 29, 2016, now Pat. No. 10,105,298.

(51) Int. Cl.

| | |
|---|---|
| *A61K 36/00* | (2006.01) |
| *A61K 33/06* | (2006.01) |
| *A61K 33/26* | (2006.01) |
| *A61K 31/045* | (2006.01) |
| *A61K 33/34* | (2006.01) |
| *A61K 36/886* | (2006.01) |
| *A61K 33/24* | (2019.01) |
| *A61K 31/255* | (2006.01) |
| *A61K 36/61* | (2006.01) |
| *A61K 31/197* | (2006.01) |
| *A61K 31/375* | (2006.01) |
| *A61K 31/4188* | (2006.01) |
| *A61K 35/06* | (2006.01) |
| *A61K 35/644* | (2015.01) |
| *A61K 33/12* | (2006.01) |
| *A61K 38/01* | (2006.01) |
| *A61K 31/355* | (2006.01) |
| *A61K 33/00* | (2006.01) |
| *A61K 31/675* | (2006.01) |
| *A61K 36/63* | (2006.01) |
| *A61K 31/185* | (2006.01) |
| *A61K 31/59* | (2006.01) |
| *A61K 33/04* | (2006.01) |
| *A61K 31/525* | (2006.01) |
| *A61K 36/82* | (2006.01) |

(52) U.S. Cl.
CPC ............ *A61K 33/06* (2013.01); *A61K 31/045* (2013.01); *A61K 31/185* (2013.01); *A61K 31/197* (2013.01); *A61K 31/255* (2013.01); *A61K 31/355* (2013.01); *A61K 31/375* (2013.01); *A61K 31/4188* (2013.01); *A61K 31/525* (2013.01); *A61K 31/59* (2013.01); *A61K 31/675* (2013.01); *A61K 33/00* (2013.01); *A61K 33/04* (2013.01); *A61K 33/12* (2013.01); *A61K 33/24* (2013.01); *A61K 33/26* (2013.01); *A61K 33/34* (2013.01); *A61K 35/06* (2013.01); *A61K 35/644* (2013.01); *A61K 36/61* (2013.01); *A61K 36/63* (2013.01); *A61K 36/82* (2013.01); *A61K 36/886* (2013.01); *A61K 38/014* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 2002/0106337 A1 * | 8/2002 | Deckers ................. | A23D 7/001 424/59 |
| 2010/0178511 A1 * | 7/2010 | Letard ................... | C07F 15/025 428/404 |

FOREIGN PATENT DOCUMENTS

| | | | | |
|---|---|---|---|---|
| DE | 10145833 A1 * | 3/2003 | ............... | A61K 8/97 |

OTHER PUBLICATIONS

Angienda et al, Potential application of plant essential oils at sub-lethal concentrations under extrinsic conditions that enhance their antimicrobial effectiveness against pathogenic bacteria. African Journal of Microbiology Research (2010), vol. 4, (Year: 2010).*

* cited by examiner

*Primary Examiner* — Qiuwen Mi
(74) *Attorney, Agent, or Firm* — Plager Schack LLP; Mark H. Plager; Kara Verryt

(57) ABSTRACT

A cream for treating the skin may include gray clay kaolin; sodium lauryl ether sulfate; blue tartrazine; sodium chloride; menthol; metabisulfite sodium; gelatin; mineral oil; olive oil; oil of cloves; water; green tea; honey; talc; and aloe vera. The cream may also include apple perfume, vitamin E, vitamin D, vitamin C, vitamin B2, vitamin B5, vitamin H, vitamin B6, and vitamin D. The cream may also include fatty acids.

10 Claims, No Drawings

ANTIMICROBIAL SKIN CREAM

RELATED APPLICATION

This application claims priority to and is a continuation of non-provisional patent application U.S. Ser. No. 15/133,172 filed on Apr. 19, 2016, U.S. Ser. No. 15/363,940 filed on Nov. 29, 2016, and U.S. Ser. No. 15/614,967 filed on Jun. 6, 2017, the entire contents of each of which is herein incorporated by reference.

BACKGROUND

The embodiments herein relate generally to skin care, and more particularly, to an antimicrobial skin cream.

The skin is the largest organ in the body, covering the surface of the human body and serving as the first line of defense in protecting the human from invasion of foreign pathogens and external injuries. In terms of wound healing, a human has the ability to self-heal a small area. However, when a person has a large area wound or poor skin restoration ability, such as those affected by diabetes, psoriasis, or leprosy, the individual may be unable to self-heal adequately, which can lead to infection.

Therefore, what is needed is a skin cream designed to improve tissue regeneration, particularly when treating skin lesions, wounds, burns, and Buruli ulcers while simultaneously having cosmetic applications as well.

SUMMARY

Some embodiments of the present disclosure include a cream for treating the skin. The cream may include gray clay kaolin; sodium lauryl ether sulfate; Brilliant blue or blue tartrazine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The cream of the present disclosure may be used to heal and rejuvenate the skin and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Gray clay kaolin
2. Sodium lauryl ether sulfate
3. Sodium chloride
4. Menthol
5. Water
6. Honey
7. Aloe Vera
8. Vitamins
9. Gelatin
10. Mineral Oils
11. Metabisulfite Sodium
12. Talc
13. Green Tea
14. Brilliant Blue or Blue Tartrazine The various elements of the cream of the present disclosure may be related in the following exemplary fashion. It is not intended to limit the scope or nature of the relationships between the various elements and the following examples are presented as illustrative examples only.

By way of example, some embodiments of the present disclosure include a skin cream comprising gray clay kaolin (chemical formula $Al_2Si_2O_5(OH)_4$); sodium lauryl ether sulfate; $CH_3(CH_2)_{11}(OCH_2CH_2)_nOSO_3Na$, wherein n is 2 or 3; blue tartrazine (chemical formula $C_{16}H_9N_4Na_3O_9S_2$); salt (NaCl); menthol ($Co_{10}H_2O$); metabisulfite sodium ($Na_2S_2O_5$); gelatin; mineral oil ($C_{102}H_{151}O_{39}N_{31}$); olive oil ($CH_3(CH_2)_7CH=CH(CH_2)_7COOH$); oil of cloves

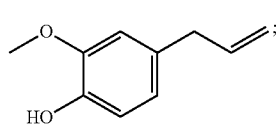

water; talc ($Mg_3Si_4O_{10}(OH)_2$); green tea (*Camellia sinensis*, which has anti-oxidant and anti-inflammatory properties and may enhance wound healing); perfume, such as apple scented perfume; honey; aloe vera; optionally, oleic acid; optionally, benzoic acid; and optionally a mixture of vitamins. The fatty acids (oil of cloves, benzoic acid, and oleic acid) may have antimicrobial properties. In some embodiments, the mixture of vitamins may comprise vitamin E; vitamin D; vitamin C; vitamin B2; vitamin B5; vitamin H; vitamin B6; and vitamin D. Gray clay kaolin is a hydrous aluminum phyllosilicate and may include mineral elements, such as Fe, Mg, Na, K, Ti, Ca, and water. The $CH_3(CH_2)_{11}(OCH_2CH_2)_nOSO_3Na$ may provide for excellent decontamination, emulsification, dispersion, wetting, solubilizing performance and foaming. It may also function as a thickener with good solvency, while also having limited irritation to skin and eyes. The skin cream may have a pH of about 7.4. Additionally, the skin cream may be green in color.

A particular embodiment of the present disclosure may comprise a batch of the cream comprising about 260 kg gray kaolin clay, about 4 kg sodium lauryl ether sulfate, about 0.8 oz (or 25 g) blue tartrazine; about 2.2 kg salt (sodium chloride—NaCl), about 100 g menthol; about 50 g metabisulfite sodium; about 95 kg gelatin; about 20 L mineral oil; about 25 L olive oil; about 25 L oil of cloves; about 20 L water; about 20 kg talc; about 5 L green tea; about ⅛ L perfume; about 5 L honey; about 10 L aloe vera; about 2,000 international units (IU) vitamin E; about 100,000 IU vitamin A; about 300 mg vitamin C; about 100 mg vitamin B2; about 250 mg vitamin B5; about 2.5 mg vitamin H; about 100 mg vitamin B6; and about 400 IU vitamin D. In embodiments, the cream may comprise about 60% gray kaolin clay.

The gray clay kaolin may comprise alumina silicate, calcium, magnesium, sodium, and potassium. The high silica content of the clay may result in the strengthening of the elastic tissues on the body, particularly in the case of contaminated blood.

The gelatin used in forming the cream of the present disclosure may be comprised mainly of collagen, which is a protein found in animal tissues, ligaments, tendons, bone, and skin. Thus, the gelatin may have healing properties, because it is a rich source of dietary collagen. The gelatin may also comprise proline, which is an amino acid that may help maintain a youthful appearance. Moreover, the gelatin may also contain Zn, Cu, and Ca.

The Brilliant blue or blue tartrazine used in the cream may be a product derived from synthetic lemon yellow and is conventionally used as a food coloring.

The mineral oil included in the cream of the present disclosure may prevent water loss from the skin. In other words, it may act as a moisturizer. In some embodiments, the mineral oil may be replaced by Vaseline. The use of mineral oil may lead to an increase in stratum corneum content by reducing trans epidermal and emolliency.

To summarize, the skin cream of the present disclosure may comprise the following:

Part 1: Gray clay kaolin

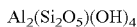

All elements listed in formula:
Al, H, O, Si—search for minerals with similar chemistry
Common Mineral Elements: Fe, Mg, Na, K, Ti, Ca, $H_2O$
The gray clay Kaolin formula is: $(Ca,Na,H)(Al,Mg,Fe,Zn)_2(Si,Al)_4O_{10}(OH)_2*H_2O$+sodium lauryl ether sulfate (shown below)

where n is 2 or 3.

Part 2: sodium laureth sulfate: $CH_3(CH_2)_{10}CH_2(OCH_2CH_2)OSO_3Na$

Part 3: water, which naturally contains minerals, such as Mg, Na, Ca, Fe, and the like Part 4: Brilliant Blue ($C_{37}H_{34}N_2Na_2O_9S_3$) or blue tartrazine ($C_{16}H_9N_{43}O_9S_2$):

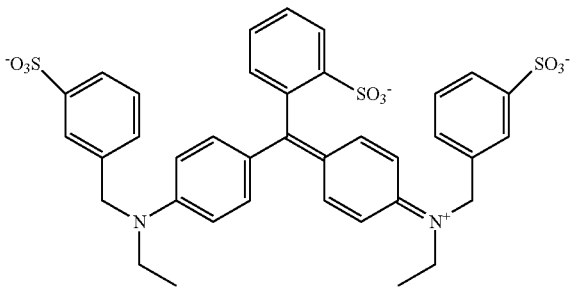

Final Product: $(Al,Zn,Fe1,67MgO,33)Si_4O_{10}(OH)_2Na^+Ca^{++})$

The weak acid character of the green clay as a Bronsted character clay arises mainly due to the dissociation of the intercalated water molecules coordinated to lauryl ether sulfate and Brilliant blue or blue tartrazine. Higher levels of Bronsted acidity are achieved when highly polarizing ions in solution have exchanged for $Na^+$, $Ca^{2+}$, in the natural clay, ions $Na^+$ present in laureth sulfate and blue tartrazine with alkali properties:

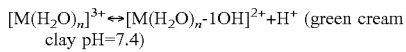

The surface area and the pore volume in the green cream clay structure may also add to the efficiency of the catalyst. Total acidity may be further increased by proton-exchange on treating the gray clay with water, sodium laureth sulfate, and brilliant blue or blue tartrazine. As a result, a corrosive acid medium is avoided, and the clay is used as a Bronsted acid.

The interlayer in the antimicrobial green clay normally contains $Na^+$, $Ca^{2+}$, and $Mg^{2+}$ that are alkali properties as compensatory cations for the charge imbalance. When the clay is dry, these cations reside in the hexagonal cavities of the silica layers. However, when the clay is treated with water, lauryl ether sulfate, and blue tartrazine, the cations may relocate themselves in the interlamellar region and become exchangeable by a variety of both metallic and nonmetallic cations, such as $H_3O^+$, $Al^{3+}$, $Fe^{3+}$ and the like.

The synthesis of the green antimicrobial cream is summarized, in detail, as follows:

Step 1: sodium lauryl ether sulfate $(CH_3(CH_2)_{10}((CH_2)O)_nSO_3Na$, where n is 2 or 3

Step 2: water containing natural minerals, such as Mg, Na, Ca, Fe, Zn, Cu, K, Mn, and the like; talc containing Mg, Mn, Ti, Fe, and Ca; and gelatin containing Zn, Cu, and Ca.

Step 3: Brilliant Blue: $C_{37}H_{34}N_2O_9S_3$, wherein Brilliant Blue is a food colorant Step 4: 2.2 kg of NaCl, the amount of which may vary depending on the use (cosmetic vs. skin infection). In this step, the solution may be blue in color.

Step 5: adding the ingredients of Steps 1-4 together with gray clay Kaolin, which has the following formula:

$(Ca,Na,H)(Al,Mg,Fe,Zn)_2(Si,Al)_4O_{10}(OH)_2*H_2O$

After mixing the ingredients, the gray color will change to green, wherein the final product is the antimicrobial green clay cream having the following formula:

$(Al,Zn,Fe_1,67MgO_{33})Si_4O_{10}(OH)_2Na^+Ca^{++}$

Processing the above by mechanical energy, i.e. by stirring and kneading the composition, results in:

$(Al,Zn,Fe+++,Fe++,67MgO_{33})Si_4O_{10}(OH)_2Na_+Ca^{++}$

Thus, the final product after stirring and kneading, which activates the hydrophilic property of the cream, is:

$(Al,Zn,Fe^{+++},Fe^{++},MgO,Mn,Cu^{++},Cu^+,Ti,Mo^+)Si_4O_{10}(OH)_2K_+Na^+Ca^{++}$ wherein the structural formula is described by the following:
interlayer position: $Na^+$, $Ca^{2+}$, $K^+$, $H_3O^+$
tetrahedral layers: Si, Al
octahedral layers: Al, $Fe^{3+}$, $Fe^{2+}$, Mg, Mn, Zn, $Cu^{2+}$, $Mo^+$, Ti.

The following crystalline oxides may have the following position in the antimicrobial cream of the present disclosure:
$SiO_2$: octahedral and $SiO^-$, $SiO_4$, wherein the amount of silicon in the final composition is about 55-65% by mass
$Al_2O_3$: tetrahedral and $AlO^-$, AlOH, AlOOH position, wherein the amount of aluminum in the final composition is about 7-27% by mass
$Fe_2O_3$: FeOOH, wherein the amount of iron in the final composition is about 10 to about 20% by mass
other oxides represent about 25% by mass of the final composition
$Na_2O^+K_2O$: octahedral
NaCl: octahedral
$ZnCl_2$, CuCl: ½ tetrahedral
$TiO_2$: octahedral
ZnO: tetrahedral
MnO: octahedral is solid crystal, $Mn^{2+}$ is a liquid
$CuO_2$: octahedral
CuO: octahedral
$K_2O$: octahedral In the composition of the present disclosure, the cations may be fixed on the surface of the colloids. Thus, the cream of the present disclosure has negatively charged surfaces between the layers described above, where the cations can be fixed. The bivalent ions ($Ca^{2+}$, $Mg^{2+}$, $Mn^{2+}$, $Fe^{2+}$) may be retained and attached on the negative inorganic colloid more strongly than the monovalent ions ($Na^+$, $K^+$). In other words, the cations may be fixed on the surface of the inorganic negative colloid. The lower hydrated ions may be more easily fixed than the strongly hydrated ions. The sodium cations of lauryl ether sulfate, which may be active in the surfactant, may exchange with the cations contained in the antimicrobial cream, causing salts to precipitate out. The salts may include calcium coceth sulfate, potassium coceth sulfate, magnesium coceth sulfate, copper coceth sulfate, manganese coceth sulfate, and zinc coceth sulfate, the structures of which are shown below.

In more detail, during Step 5 the green clay reacts as Bronsted character, and the materials react to the balance and stability of every element in an antimicrobial concept. The hydrogen protons ($H^+$) are attracted to the negatively charged clay surface to varying degrees, as shown below:

$$[M(H_2O)_n]^{3+} \leftrightarrow [M(H_2O)_n\text{-}1OH]^{2+}+H^+, \text{ where green cream clay has a pH of 7.4}$$

Thus, the change to a green color is caused by the transformation of $Fe^{2+}$ to $Fe^{3+}+e$. In other words, the color of the product, the antimicrobial clay, is green because of the combination of the two forms of iron. Thus, the antimicrobial green clay is the product of mixed valence condition of formation. The iron is reduced from $Fe^{3+}$ and enters into a silicate mineral structure. In general, iron would rather be an oxide when it is in the trivalent state, at which time it is reduced to the divalent state under the surface or near the surface. The silicate, sulfide, or carbonate hides when the silicate is oxidized, and the iron begins to group together in oxide clumps, eventually exiting the silicate structure. The production of trivalent oxidized iron typically results in a yellow, brown, or orange color. However, with the presence of Brilliant Blue or Blue Tartrazine, the color becomes green. The resulting final product has the following chemical structure: $(Al,Zn,Fe1,67MgO,33)Si_4O_{10}(OH)_2Na^{30}\ Ca^{++})$.

The following is also present:

$$2FeO+\tfrac{1}{2}O_2(g) \rightarrow Fe_2O_3$$

$$(Al,Zn,Fe^{3+},Fe^{2+},67MgO_{33})Si_4O_{10}(OH)_2Na^+Ca^{2+}$$

$$(Al,Zn,Fe^{3+},Fe^{2+},MgO,Mn,Cu^{2+},Cu^+,Ti,Mo^+)Si_4O_{10}(OH)_2K^+Na^+Ca^+$$

The present formula represents the final product by mass and composition. The Galenic structure, properties, and parameters for the formation of ortho-silicic acid may also be represented. During the synthesis process, the behavior of silica starting from synthesis process until the formation of ortho-silicic is explained.

During the synthesis process, talc ($Mg_3Si_4O_{10}(OH)_2$) may also be added, as described above. As a result, the following reactions may occur:

$$Mg_3Si_4O_{10}(OH)_2(s)+Al_2Si_2O_5(OH)_4(s)+15H_2O \rightarrow 6(H_4SiO_4)(s)+2Al(OH)_3+3Mg(OH)_2$$

During this reaction, the formation of ortho-silicic acid, aluminum hydroxide, and magnesium hydroxide may occur, provided by the complete hydrolysis of Kaolin ($Al_2Si_2O_5(OH)_4$) and talc and activated by the presence of a sufficiet amount of sodium chloride, lauryl ether sulfate, and fatty acids. In the presence of Blue Tartrazine and vitamins, this reaction may result in a gradual solubility of silicon and the generation of ortho-silicic, organic silicic, aluminum hydroxide, and magnesium hydroxide.

The solubility and hydrolyzation of mineral silicon (Kaolin) may generate the organic silicon compound by alkylation, hydrolyzation, dehydration, condensation, chelation, and cation exchange. Obviously, the solubility of silica in water is a basic factor in the behavior of silica acid. When solid phase silica is in contact with water, small amount of silica dissolve and enter the aqueous phase. The dissolution and deposition of silica acid in water involves hydration and dehydration. The synthesis process of the cream includes the transformation of mineral compound in an organic compound. The process may generate the activities and the presence of silicon organic such as: organic silicon salt, silicon hybrid, silane coupling agent, organic Tri-silicon salt, silanol, di-silanol, dialkoxide salt of salt of organic silicon, and ester salt silanol to form ortho-silicic acid, which may provide strong biological stability, skin disease healing processes, and wound healing power as shown below:

$$(SiO_2)_n+2H_2O \leftrightarrow (SiO_2)_{n-1}+Si(OH)_4, \text{ wherein } n>1.$$

The formation of $Si(OH)_4$ is shown further below:
(a) Hydrolyze $Si^{4+}$ with water dissociation:

$$Si^{4+}+H_2O \rightarrow Si(OH)^{3+}+H^+$$

$$Si(OH)^{3+}+H_2O \rightarrow Si(OH)_2^{2+}+H$$

$$Si(OH)_2^{2+}+H_2O \rightarrow Si(OH)^+ +H^+$$

$$Si(OH)^+ +H_2O \rightarrow Si(OH)_4+H^+$$

(b) Thus, the result is:

$$Si^{4+}+4H_2O \rightarrow Si(OH)_4+4H^+$$

$$H^+ +OH^- \rightarrow H_2O(l), \text{ wherein the pH=7.4}$$

The reactivity and the supramolecular properties of the salts and esters of the ortho-silicic acid, both during the phase in solution (aqueous or organic) and the solid phase or liquid crystal, is explained below.

Taking into account the reactivity of ortho-silicic acid, several types of noncovalent saline interactions allow the cohesion of supramolecular assemblies, wherein the affinities are based on electrostatic forces softened by the presence of surfactants, such as lauryl ether sulfate. The supramolecular properties of ortho-silicic in the antimicrobial cream of the present disclosure are based on non-covalent interactions, the properties of which are different between two or more molecules. However, there are also ion-dipole interactions, arising from electrostatic interactions between ions and a free electron pair of a polar molecule. Thus, the antimicrobial cream includes the presence of hydrogen bonds, dipole-dipole interactions, stacking pi, and stacking T.

In the present disclosure, non-covalent intermolecular forces include electrostatic interactions, ion-dipole interactions, and dipole-dipole interactions, including Van der Waals forces, and the like. Thus, there lays a field of supramolecular chemistry, which uses intermolecular bonding through non-covalent interactions, allowing individual molecules to be held together with non-covalent intermolecular forces to form a bigger unit, called a supramolecule, where the individual molecules have their own organization, stability, and tendency to associate or isolate.

For example, the reactions may include the interaction of silicon ions and the following as shown:

(1) Lauryl ether sulfate: $CH_3(CH_2)_{11}(OCH_2CH_2)_n OSO_3Na$, where n is from about 2 to about 3

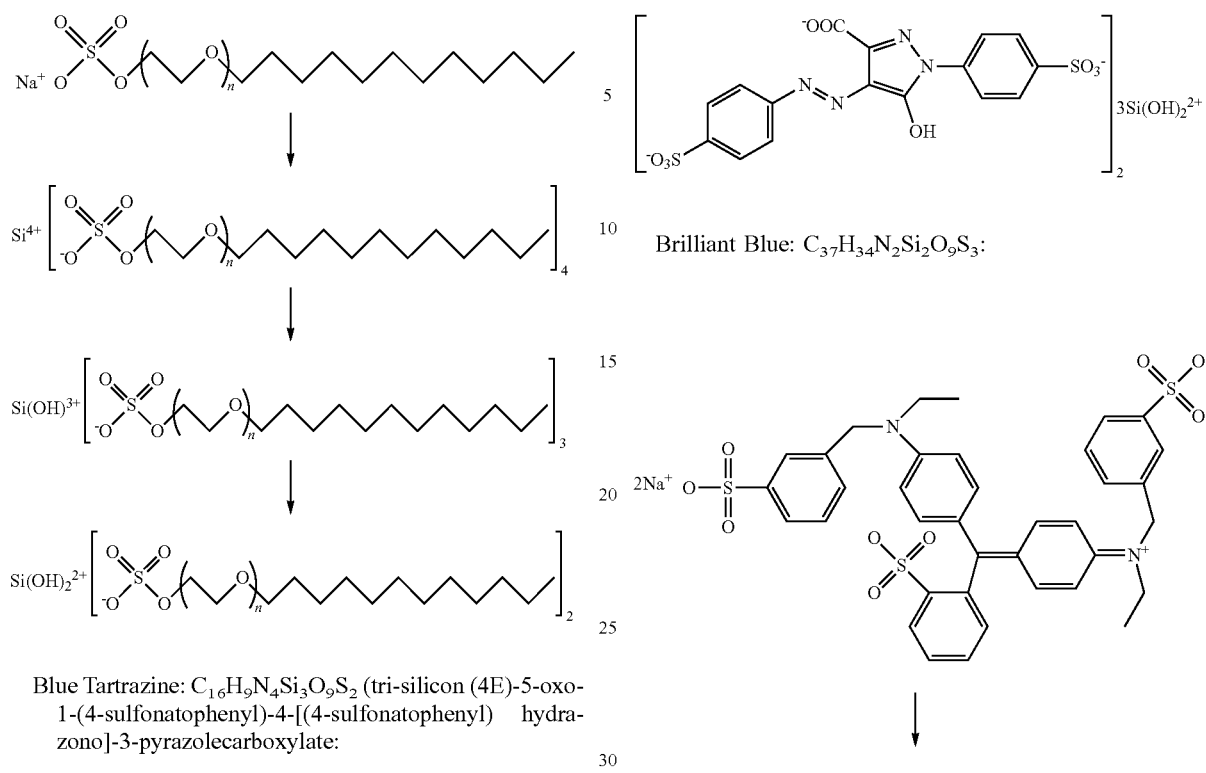
Blue Tartrazine: $C_{16}H_9N_4Si_3O_9S_2$ (tri-silicon (4E)-5-oxo-1-(4-sulfonatophenyl)-4-[(4-sulfonatophenyl) hydrazono]-3-pyrazolecarboxylate:
Brilliant Blue: $C_{37}H_{34}N_2Si_2O_9S_3$:
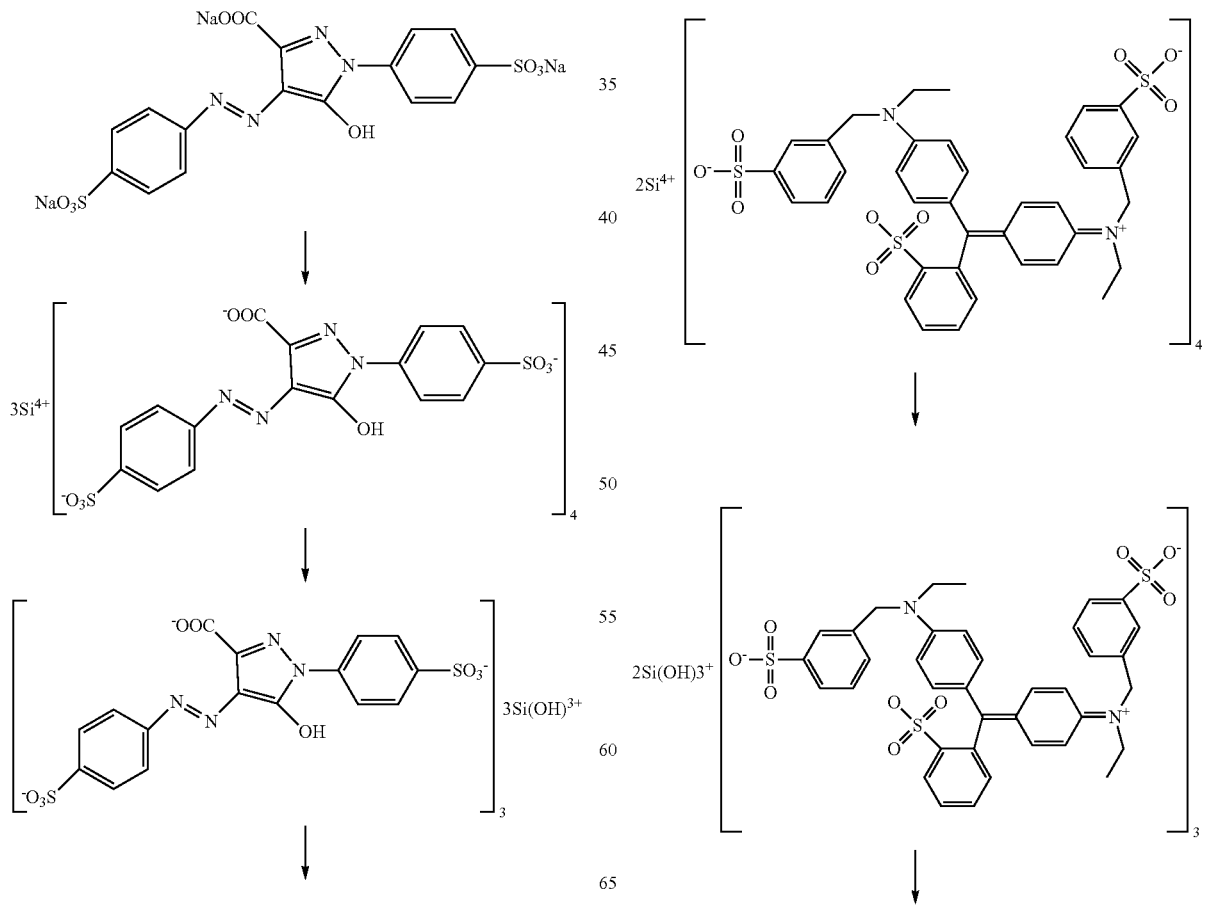

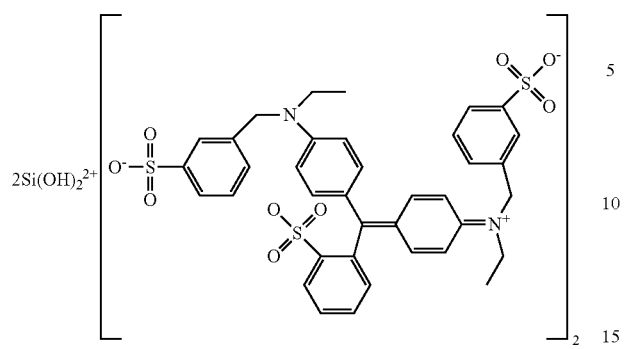

With fatty acids: Oleic Acid $CH_3(CH_2)_7CH=CH(CH_2)_7COOH$

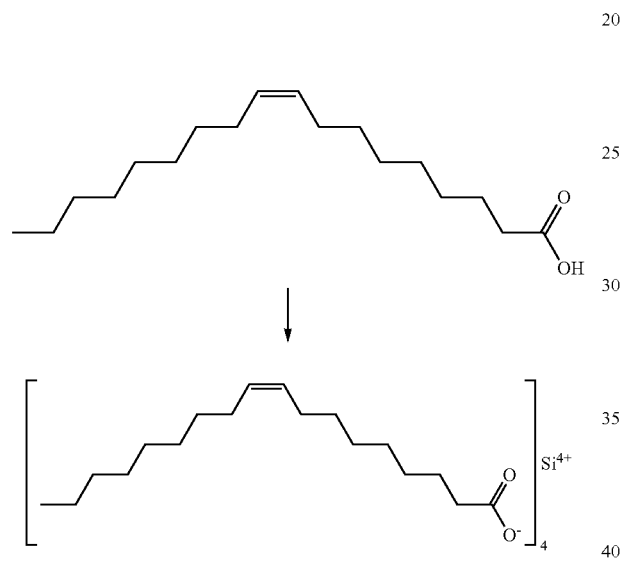

Silicon organic Oligomer (4) Oleate salt/supramolecular assemblies

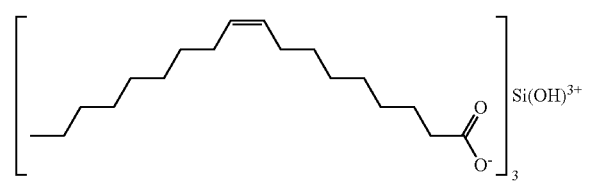

Hydroxy-silicon oligomer (3) oleate salt or silanol oligomer (3) oleate salt

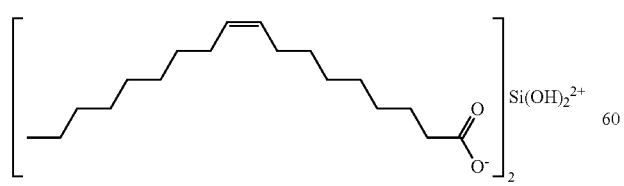

Di-hydroxy-silicon oligomer (2) oleate salt or silanediol oligomer (2) oleate salt/supramolecular assemblies, reaction activated by the presence of NaCl, AlCl$_3$, H$_2$O With fatty acids: Oil clove $C_{10}H_{12}O_2$ or $C_7H_{12}CN_3O_2$

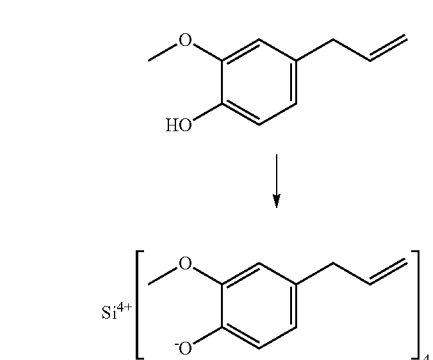

Salt/Organic Silicon Calix (4) Eugenate Supramolecular Assemblies

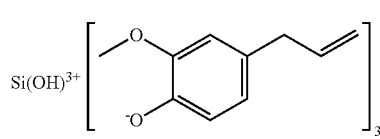

Salt/Hydroxy-Silicon Calix (3) Eugenate or Salt/Silanol Calix (3) Eugenate

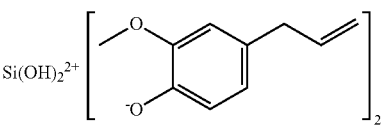

Salt/Di-Hydroxy-Silicon Calix (2) Eugenate or Salt/Silanediol Calix (2) Eugenate In the antimicrobial cream of the present disclosure, the supramolecular effects is activated by the presence of silicon, NaCl, the colloid inorganic, AlCl$_3$, H$_2$O, lauryl ether sulfate, Brilliant Blue or blue tartrazine, which are polystyrenes:

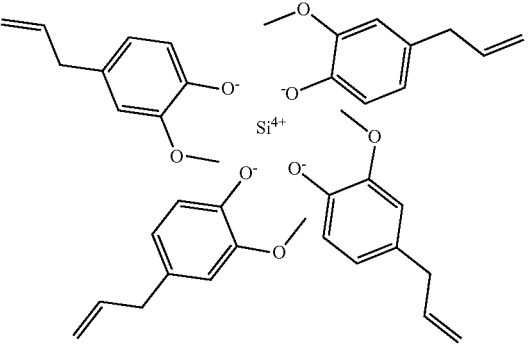

11
Salt/Organic Silicon Calix (4) Eugenate Supramolecular Assemblies

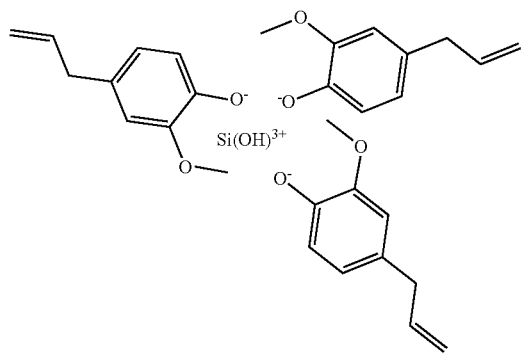

Salt/Hydroxyl-Silicon Calix (3) Eugenate or Salt/Silanol Calix (3) Eugenate

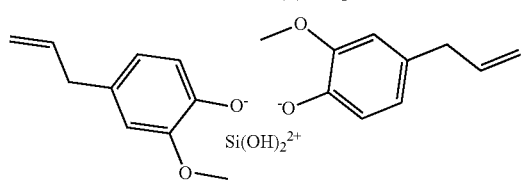

12
Salt/Di-Hydroxy-Silicon Calix (2) Eugenate or Silanediol Calix (2) Eugenate Salt

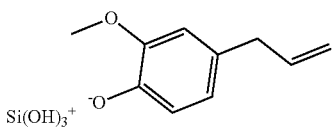

Salt/Tri-Hydroxy-Silicon

Calix (1) eugenate or salt/silanetriol calix (1) eugenate in the supramolecular assemblies Process of mesomeric effect interaction between eugenol and ortho-silicic acid in the cream of the present disclosure:

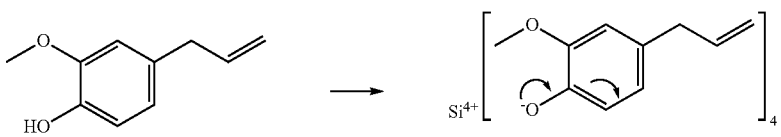

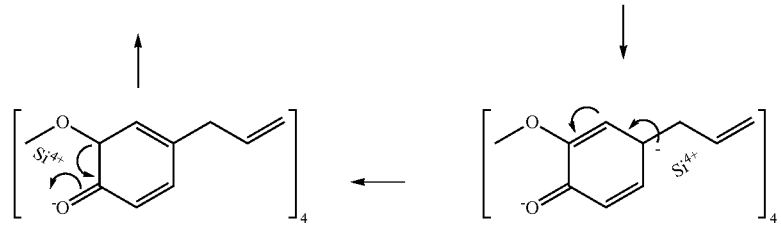

Salt/Silicon Organic Calix (4) Eugenate in Supramolecular Assemblies in Mesomeric Effect: Resonance Structure

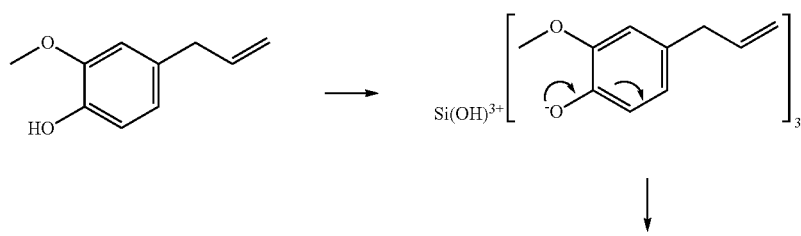

-continued
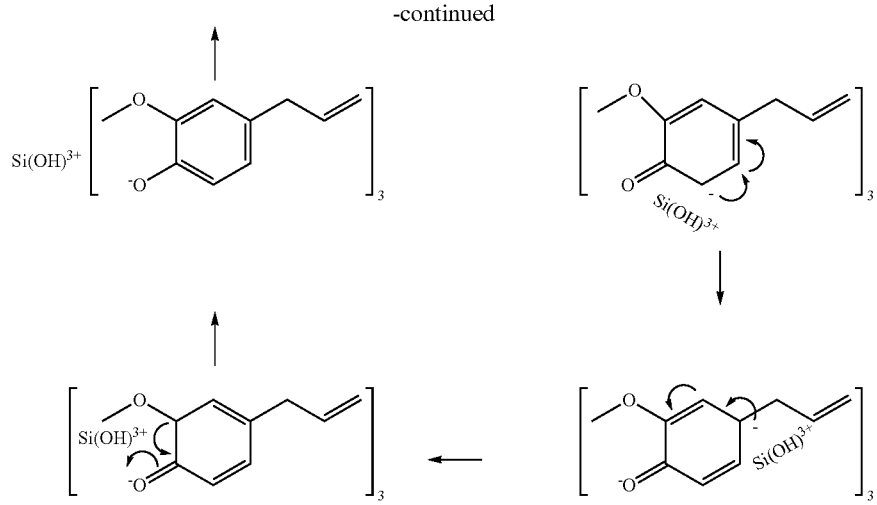
Salt/Hydroxy Silicon Calix (3) Eugenate or Silanol Calix (3) Eugenate in Supramolecule Assemblies: Resonance Structure
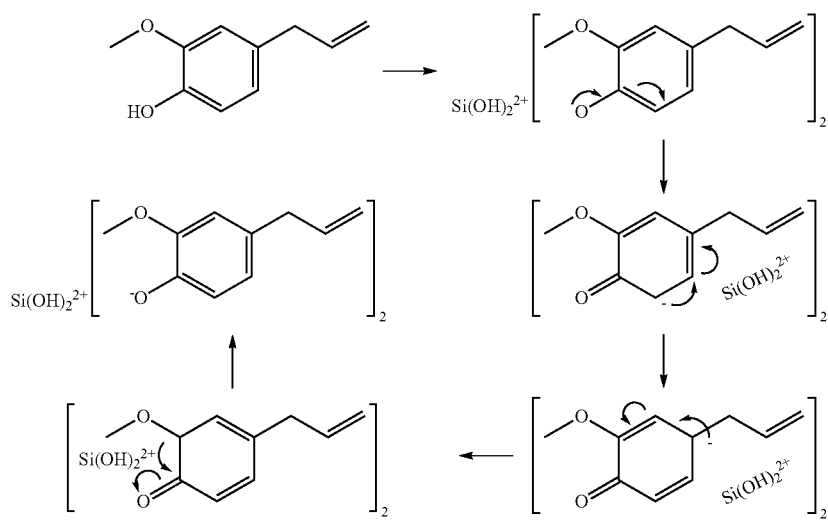
Salt/Dihydroxy-Silicon Calix (2) Eugenate or Silanediol Calix (2) Eugenate in the Supramolecular Assemblies in Mesomeric Effect: Resonance Structure
Menthol reactivity:
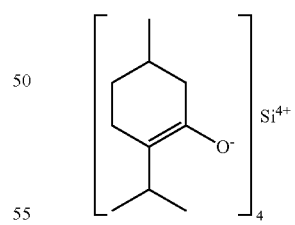
Salt/Silicon Organic Calix (4) Menthenolate
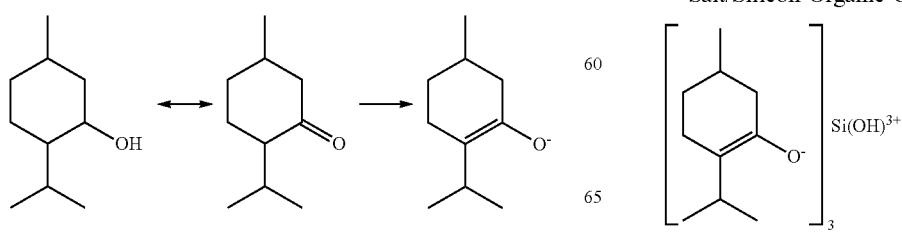

Salt/Hydroxyl-Silicon Calix (3) Menthenolate or
Salt/Silanol Calix (3) Menthenenolate

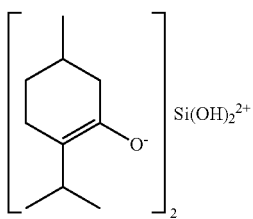

Salt/Di-Hydroxy-Silicon Calix (2) Menthenolate or
Salt Silandiol Calix (2) Menthenolate Sodium Bisulfite (NaHSO$_3$) Reactivity:

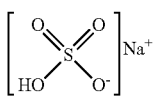

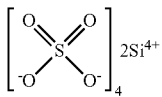

Salt/Di-Silicon Organic Oligomer (4) Sulfite

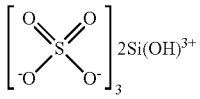

Salt/Hydroxyl-Di-Silicon Oligomer (3) Sulfite or
Salt/Di-Silanol Oligomer (3) Sulfite

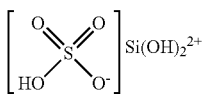

Salt/Di-Hydroxy-Silicon Oligomer (2) Bisulfite or
Salt/Silandiol Oligomer (2) Bisulfite

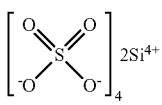

Salt/Di-Silicon Organic Oligomer (4) Sulfite

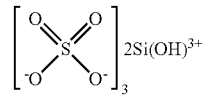

Salt/Hydroxyl-Di-Silicon Oligomer (3) Sulfite or
Salt Di-Silanol Oligomer (3) Sulfite

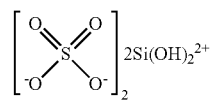

Salt/Di-Hydroxy-Di-Silicon Oligomer (2) Sulfite or
Salt Di-Silanediol Oligomer (2) Sulfite Stability of Ortho-Silicic Acid in the Anti-Microbial Cream:

In concentrated solutions, ortho-silicic acid (H$_4$SiO$_4$) has to be stabilized to avoid its polymerization into poly-silicic acids and eventually into silica gel, resulting in a decreased silicon bioavailability. Therefore, the salt (NaCl), lauryl ether sulfate, Blue Tartrazine, or brilliant blue is used to provide stability by providing ester, dimer ester, biochemical, and salt. Also, chloride compounds, such as NH$_4$Cl, NaCl, MgCl$_2$, and CaCl$_2$ stability the ortho-silicic acid to maintain its bio-organic chemistry structure. Thus, all stable biological compounds in the antimicrobial cream helps stabilize ortho-silicic acid.

Additionally, in the cream of the present disclosure, the organic silicon may provide thermodynamic stability. The negative charge is developed from substitution of Al$^{3+}$ for Si$^{4+}$ (in tetrahedral sites) and Mg$^{2+}$ for Al$^{3+}$ (in octahedral sites). Cations, such as K$^+$, Na$^+$, Ca$^{2+}$, and NH$_4^+$ are attracted to the interlayer, forming a weak surface bond. As such, the structure of water in the interlayer expands the clay to accommodate additional compounds, including neutral and negatively charged species with ionic and hydrogen bonds. In this stage of the reaction, crystalline swelling and osmotic swelling may be observed with the presence of sufficient amounts of sodium chloride.

Hydrolysis and dehydration performed by ortho-silicic acid both deal with water and other molecules, but in very different ways. Both have a reverse reaction in relation to each other and vice versa. These processes involve the formation of polymers, esters, ester alkyl silanol, and ester di-alkyl silanol, which are linked together by supramolecular assemblies and hydrogen bonds. Silicon ions (Si$^{4+}$) may be present, because of the gradual solubility of silicon followed by hydrolysis, dehydration, and methylation, which create a compound and complex by electrostatic attraction affinity with the reactivity of tectosilicate and organic silicon supervised by a hydrogen bond during the crystalline and osmotic swelling. Moreover, the ortho-silicic ester silanol compound, coupling agent, di-alkoxy, and ester salt provided by Si$^{4+}$, Si(OH)$^{3+}$, Si(OH)$_2^{2+}$ are more stable than those provided by Si(OH)$_3^+$ because of electrostatic repulsion. Therefore, because of the inorganic colloid, the polystyrene styrene sulfonate (Brilliant Blue or Blue Tartrazine and lauryl ether sulfate) do not stabilize; rather, they require more affinity to be stable in the field of supramolecular stability and, thus, there are electrostatic repulsions.

The least stable compound may be with $Si(OH)_3^+$, such as:

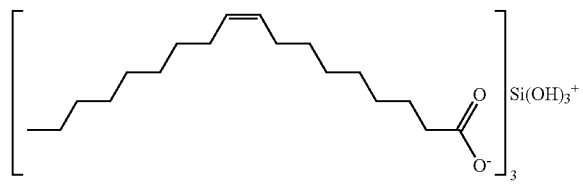

Salt/Tri-Hydroxy-Silicon Oligomer (3) Oleate or
Salt/Silane-Triol Oligomer (3) Oleate Aluminum Hydroxide Reactivity in the Antimicrobial Cream:

The ability of aluminum hydroxide to neutralize acids makes it a natural choice as an antacid. It also has a stimulating effect on the immune system. Moreover, it reacts as an emollient. The emollients softens the skin. It is a hygroscopic humectant, meaning that it maintains the water content in its packaging and on the skin. Finally, aluminum hydroxide is a pacifier. Aluminum hydroxide may also be used for antigen absorption, because aluminum has a strong tendency to hydrolyze in a solution:

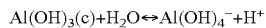

wherein $H^+$ is attracted by a anionic compound, such as lauryl ether sulfate and Blue Tartrazine or a negative inorganic colloid and may combine with $(OH)^-$ to obtain $H_2O$. Thus, an equilibrium may be present.

(2) The formation of ortho-silicic acid in the anti-microbial cream of the present disclosure may occur with the influence of several conditions:

Ortho-Silicic Formation by Hydrolyzation of Stress Stability:

A chemical system is thermodynamically stable when it is at its lowest energy level or in chemical equilibrium with its environment. The tectosilicate is basically made up of $SiO_4^{4-}$ tetrahedral units linked in their corners by Si—O—Si bonds. The Si—O bonds may be under mechanical stress and dissolve into $Si^{4+}$ with the presence of Brilliant Blue and lauryl ether sulfate. The addition of talc may provide the additional silicon and magnesium. As mentioned, the Si—O bond may be under mechanical stress and, if it can be broken, a microcrack in the silicate may occur. Water molecules in the vicinity of the stress point will be attracted to the Si—O bond so that its oxygen bonds to the silicon via the oxygen lone pairs. Also, one of its hydrogens can hydrogen bond to the bridging oxygen. Next, there is a simultaneous transfer of protons and electrons. Thereafter, the new bonds are formed—one between oxygen and silicon and the others between hydrogen and oxygen. Finally, the original bond between oxygen and silicon is destroyed. The final step is breakage of the hydrogen bond and the transferred hydrogen to give an Si—OH on each fractured surface, leaving multiple $H_4SiO_4$ (s) compounds. Thus, the combination of a weakened bon and constant stress created by the lauryl ether sulfate and Blue Tartrazine may lead to microcrack extension.

Ortho-Silicic Formation by the Process Stimulation by the Addition of Talc Powder:

In the antibacterial cream of the present disclosure, the silicon may be found in crystallized form. Hydrolysis may occur under neutral conditions or slightly basic conditions (at a pH of 7.4). Therefore, with the addition of talc powder, which provides silicon ($Si^{4+}$) and magnesium, in the presence of an anionic compound (Brilliant Blue or Blue Tartrazine and lauryl ether sulfate), the silicon ($Si^{4+}$) from aluminosilicate and talc occurs and splits the water into $H^+$ and $OH^-$. Therefore, the process may lead to the formation of silicic acid, which can be represented by thinking of the silicon as $Si^{4+}$ ions even though the silicon is actually at the center of a tetrahedron of atoms, which is covalently bonded. Also, the isomorphism in the tetrahedral layers the $Si^{4+}$ from aluminosilicate which occurs may hydrolyze $SiO_2$, splitting it into $Si^{4+}$ and $O^{2-}$, forming a stabilized compound of ortho silicic acid in the presence of stabilizing agents, such as ammonium chloride ($NH_4Cl$), all coceth sulfate, and metalloprotein compounds generated by Blue Tartrazine. Aqueous sodium silicate combined with water causes acidification, which causes the formation of mono $Si(OH)_4$. Specifically, water assists the formation of a $Si(OH)_4$ molecule from a single $SiO_2$ molecule. The dynamics of the dissociation of water molecules and the formation of Si—OH are ideal model systems for understanding the basic nature of hydrogen bonding, solvation shell structure, proton or hydrogen atom motion, and the interplay between structure and dynamics.

The formation of ortho-silicic acid $Si(OH)_4$ occurs with dissociation ($H_2O \leftrightarrow H^+ + OH^+$) on the tetrahedral layer during the hydrolyzation process of the clay. Also, crystalline swelling and osmotic swelling may occur because of a sufficient amount of sodium chloride being present. The isomorphism substitution process may be observed. Upon dissolution, the following equilibrium is formed:

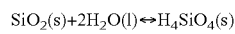

wherein the $SiO_2$ is splitting into $Si^{4+}$ and $O^{2-}$ among the potential energy of attraction, repulsion, and resistance. Attraction is between the negative colloid and cations, and repulsions are between the anions and negative colloids. In the present disclosure, the silicon ($Si^{4+}$) from aluminosilicate is a tetravalent ion and, during osmotic swelling, may form ortho-silicic acid by cation exchange with Brilliant Blue and lauryl ether sulfate, wherein strong electrostatic attractions and hydration repulsions force and control crystallinity. The silicon ($Si^{4+}$) ions are attracted from the crystalline site; however, silicon is actually at the center of a tetrahedron of atoms, which are covalently bonded. Therefore, silicon is attracted and split by the inorganic colloids, Brilliant Blue and lauryl ether sulfate, which are negatively charged, forming $Si^{4+}$.

The addition of talc powder on the clay facilitates the hydrolysis of silicon in the presence of Blue Tartrazine (an anionic polystyrene compound) and lauryl ether sulfate (an anionic polystyrene surfactant), splitting the silicon by interelectron exchange, creating $Si^{4+}$ with a crystalline and osmotic swelling impact with large amounts of sodium chloride. The talc may also provide $Mg^{2+}$. The water molecules may be electrically charged and behave like dipoles. Moreover, the following equilibrium may be observed, wherein the balance contains silicic acid, a weak acid that also forms during silicon aluminosilicate and talc hydrolysis:

Ortho-Silicic Formation by the Physical Properties of Gelatin Through the Dynamics of Water:

The properties of gelatin as a typical rigid-chain high molecular weight compound are, in many respects, similar to those of rigid-chain synthetic polymers. Gelatin exhibits essentially the same common properties typical of polymeric substances, which is not the case with native collagen. Thus, in a similar way to linear-chain synthetic polymers, in aqueous solutions at elevated temperatures gelatin macromolecules assume the conformation of a statistical coil. Under specific conditions (temperature, solvent, pH) gelatin macromolecules can display a flexibility sufficient to realize a wide variety of conformations. This makes it possible to vary all the gelatin characteristics depending on its molecular structures. Obviously, gelatin is a biopolymer, wherein its specific interaction with water is different than that observed with synthetic hydrophilic polymers. This peculiarity governs the structural and physica-mechnical properites of gelatin in the solid state in the antimicrobial cream. Water sorption by gelatin depends on a number of factors, both common to all substances and specific for gelatin and related polymers.

In the present disclosure, the sorption capacity of gelatin depends substantially on the amount of sodium chloride and the pH, which is 7.4 and increases during osmotic and crystalline swelling processes with ionization of the cation imbalance of the dissociating groups. The factors include the following:

(1) Water bound by high-energy sorption center: this water occurs inside the collagen triple helix and plays a major role it its stabilization by intramolecular hydrogen bonds.

(2) Water sorption by polar groups of gelatin and collagen macromolecules: this water is also strongly bound with the proteins by H-bonds and is located outside the helical fragments, but it also contributes substantially to the stabilization of the collagen helical structure. Water sorption by proteins and silicon ($SiO_2(s)$) in the antimicrobial cream of the present disclosure activates the formation of ortho-silicic acid mixed with polymolecular layers of protein proceeding from the total amount of water bound with gelatin and collagen. Gelatin is hygroscopic and hydrophilic. Increasing its sorption character and activating the formation of orthosilicic acid may be achieved with the presence of other hydrophilic and hygroscopic compounds, such as sodium chloride (NaCl), aluminum hydroxide ($Al(OH)_3$), iron(III) chloride ($FeCl_3$), and calcium chloride ($CaCl_2$).

The above properties of water sorption in the present disclosure (hydrolyzation and dehydration) deal with water and other molecules, such as silicon, but in very different ways. Both have a reverse reaction in relation to each other, and they perform the cycle for the formation of ortho-silicic acid. Moreover, hydrophilic and hygroscopic compounds, such as sodium chloride (NaCl), aluminum hydroxide ($Al(OH)_2$), iron (III) chloride ($FeCl_3$), calcium chloride ($CaCl_2$), and gelatin, improve and accelerate the sorption capacity of the antimicrobial cream for the formation of ortho-silicic acid. Specifically, the gelatin participated in the formation of the ortho-silicic acid by hydrolyzing silicon when it is added to the antimicrobial cream at about 37° C., maintaining the inherent physical and chemical characteristics of the macromolecule by hydrolyzation and dehydration and allowing the cream to acquire new properties by lowering its weight.

Ortho-Silicic Formation by Attraction and Hydrolyzation of Silicon by an Emulsification Process of Polar and Anionic Compounds (Blue Tartrazine and Lauryl Ether Sulfate):

When lauryl ether sulfate, which is commonly known as soap or detergent, is mixed with water, fatty acid(s), and silicon ($SiO_2$), the lauryl ether sulfate molecules surround the oil droplets. The oil or grease is "dissolved" in the alkyl groups of the soap molecules, while the ionic end allow the micelle to dissolve in water. As a result, the oil droplets are dispersed throughout the water. The silicon ions ($Si^{4+}$) are attracted by an anionic compound (lauryl ether sulfate). Therefore, the anionic compound will react with silicon ions in the water and can form insoluble precipitates and organic and anti-microbial compounds having healing abilities. This process may be activated by an anionic polystyrene compound, such as Blue Tartrazine, as shown below:

$$(SiO_2)_n+2H_2O \leftrightarrow (SiO_2)_{n-1}+Si(OH)_4\text{, wherein } n>1$$

Please note that in the above $SiO_2$ is solid silica or polysilicon acid in water The formation of $Si(OH)_4$ is shown further below:

(a) Hydrolyze $Si^{4+}$ with water dissociation:

$$Si^{4+}+H_2O \rightarrow Si(OH)^{3+}+H^+$$

$$Si(OH)^{3+}+H_2O \rightarrow Si(OH)_2^{2+}+H$$

$$Si(OH)_2^{2+}+H_2O \rightarrow Si(OH)_3^{+}+H^+$$

$$Si(OH)_3^{+}+H_2O \rightarrow Si(OH)_4+H^+$$

(b) Thus, the result is:

$$Si^{4+}+4H_2O \rightarrow Si(OH)_4+4H^+$$

$$H^++OH^- \rightarrow H_2O(l)\text{, wherein the pH}=7.4$$

Ortho-Silicic Formation by Hydrolyzation and Dehydration Through the Dynamic of Water and Hydrogen Bond During Crystalline and Osmotic Swelling:

The water molecules are electrically charged and behave like dipoles. The solubility of silica in water is a basic factor in the behavior of silicic acid. When solid phases of silica are in contact with water, small amounts of silica dissolve and enter the aqueous phase. The dissolution and deposition of silica in water involves both hydrogen and dehydration reactions, as shown below:

$$(SiO_2)n+2H_2O \leftrightarrow (SiO_2)_{n-1}+Si(OH)_4\text{, wherein } n>1$$

and $SiO_2$ means solid silica or polysilicon acid in water

In the present disclosure, sodium chloride (NaCl), aluminum hydroxide ($Al(OH)_3$ (aq)), iron (III) chloride ($FeCl_3$ (aq)), and calcium chloride are extremely hygroscopic and extract water from their surroundings, thus forming a stabilized silica and hydrolyzing a silicon compound into ortho-silicic acid in the presence of lauryl ether sulfate (and anionic surfactant) and Blue Tartrazine (an anionic and polystyrene compound) and water. Moreover, in chemical analyses of natural water, dissolved silicon ($Si^{4+}$) is commonly listed as $SiO_2$ (aq). However, the entity in the solution is actually $Si(OH)_4$, with a weight of 96 g. Obviously, $Si^{4+}$ is dissolved as a hydroxocomplex, and $Si(OH)_4$ is the formula that best represents the nature of that complex, because $SiO_2$ is merely a lineal molecule.

Water can reduce the strength of the Si—O bond lengths of 2.87 $a_0$ in silica. The water molecule has an O—H bond length of 1.83 $a_0$ and an H—O—H bond angle of 104.3°. In the cream of the present disclosure, when the water molecule is attached to $SiO_2$, the binding energy between the two molecules (i.e., the solvation energy) is about 1.5 ev. This energy is obtained based on a structure on a structure in which the water does not dissociate in the principle of water sorption induced by the physical condition of gelatin (exercising pressure) in the presence of a hygroscopic agent, such as sodium chloride (NaCl), aluminum hydroxide (Al(OH)$_3$), iron (III) chloride (FeCl$_3$), and calcium chloride (CaCl$_2$), contained in the anti-microbial cream. The water molecule induces a dipole moment in SiO$_2$ such that the SiO$_2$ molecule is no longer linear, but has a bonding angle of 158.6°. The Si—O interaction also modifies the H$_2$O structure. The difference in electronegativities between oxygen and hydrogen atoms create partial negative and positive charges, respectively, on the atoms.

Water molecules attract or are attracted to other polar molecules. By the principle of water sorption in the presence of hydroscopic agent, such as sodium chloride (NaCl), gelatin participates (exercising pressure) in the formation of ortho-silicic acid by hydrolyzing silicon when it is added to the antimicrobial cream at 37° C. in the presences of a hygroscopic component, such as $CaCl_2$, ($Na^+$, $Cl^-$), $Al(OH)_3$, $FeCl_3$, and gelatin, as shown below:

$$SiO_2+H_2O \rightarrow SiO_2—H_2O$$

$$SiO_2—H_2O+H_2O \rightarrow SiO_2—(H_2O)_2$$

$$SiO_2—(H_2O)_2+H_2O \rightarrow SiO_2—(H_2O)_3$$

$$SiO_2—(H_2O)_3+H_2O \rightarrow SiO_2—(H_2O)_4$$

$$SiO_2—(H_2O)_4 \rightarrow SiO_3H_2(H_2O)_3$$

$$SiO_3H_2(H_2O)_3+H_2O \rightarrow Si(OH)_4+(H_2O)_3$$

$$SiO_3H_2(H_2O)+2H_2O \rightarrow Si(OH)_4+(H_2O)_4$$

$$H^++OH^- \rightarrow H_2O(l), \text{ wherein the pH=7.4}$$

Thus, water plays an important role during crystalline and osmotic swelling and leads to the formation of ortho-silicic acid $Si(OH)_4$ molecules through the analysis of the structure and dynamics of $SiO_2$ in water. The movement of cations may be followed by measurement of electrical conductivity. When the cations are hydrated, the layers may be spread apart to allow the cation to pass from one site to another, and an electrical current may be measured. The current may be a function of the compensation cation and the interaction between the clay surface. The hydrolysis of silicon ($SiO_2$) is accelerated by the presences of sufficient amounts of sodium chloride (NaCl) and the presence of $CaCl_2$, $FeCl_3$, and $Al(OH)_3$. When the water ionizes in the presence of the biologically stable anionic organic compound salts (lauryl ether sulfate and brilliant blue or blue tartrazine, the H—O—H bond angle becomes 110.6°, which is almost 9% larger than the angle in an isolated water molecule, and the O—H bond length increases about 3%, all of which is due to osmotic and crystalline swelling in the presence of inorganic colloids.

Formation of Ortho-Silicic Acid by Dehydration:

The ortho-silicic acid ($H_4SiO_4$) has the capacity to surrender an $H^+$ or to dehydrate by the attraction of $H^+$ performed by a biologically stable anionic organic salt compound, such as a polystyrene sulfonate (lauryl ether sulfate, brilliant blue, or blue tartrazine). Moreover, ortho-silicic acid ($H_4SiO_4$) has the capability to dehydrate and, thus, it is commonly used to surrender $H^+$. In this step, $H^+$ is attracted by the inorganic negative colloid and lauryl ether sulfate (an anionic and polystyrene surfactant) and Blue Tartrazine (an anionic and polystyrene compound) to create a stable compound with biologically stable ions that behave like an acid.

$Si(OH)_4$ and $H_4SiO_4$ are commonly referred to as silicic acid or ortho silicic and their interaction modifies the structure of water. In the present disclosure, the following process acts through the dynamics of water in combination with the antimicrobial cream:

$$Si_2O(OH)_6 \rightarrow H_6Si_2O_7 \text{ wherein the pH is 7.4}$$

A first $H^+$ dissociates, resulting in:

$$SiO(OH)_3^- \rightarrow H_3SiO_4^-$$

A second $H^+$ dissociates, resulting in:

$$SiO_2(OH)_2^{2-} \rightarrow H_2SO_4^{2-}.$$

A $Si(OH)_4$ tetrahedra then combines to make a polynuclear complex or dimer, as opposed to the mononuclear complex. The bridging $O^{2-}$ is bonded to two $Si^{4+}$ and loses $H^+$. The $H^+$ combines with $OH^-$ to form $H_2O$, indicating that the formation of the dimer is a dehydration reaction. Moreover, $H_2SiO_3$ is present, where $Si^{4+}$ is in three fold, rather than four fold coordination. Metasilicic acid is thus the silicic analogue of carbonic acid ($H_2CO_3$), and is a less hydrous form of silicic acid. Additionally, because $H_4SiO_4 \rightarrow H_2SiO_3+H_2O$, as described above, disilicic ($H_2Si_2O_5$) is a dimer of metasilicic acid, $H_2SiO_3$.

In the present disclosure, ortho-silicic acid is present in dilute and stable concentrations with the presence of ammonium chloride ($NH_4Cl$), Brilliant Blue or Blue Tartrazine, and lauryl ether sulfate, which are salt amino sources, and sodium chloride. Therefore, in the concentrated solution, ortho-silicic acid ($H_4SiO_4$) has to be stabilized to avoid its polymerization into polysilicic acids, resulting in a decreased silicon bioavailability.

During dehydration, the complex orth-silicic may surrender $H^+$, resulting in:

$$H_4SiO_4(s)+H_2O(l) \leftrightarrow H_3O^+(aq)+H_3SiO_4^-(aq)$$

$$H_4SiO_4(aq) \leftrightarrow H_3SiO_4^-+H^+.$$

In the present disclosure, there are processes (hydrolysis, dehydration, emulsification, and talc addition, that play vital roles in the biosynthesis of ortho-silicic acid.

Impact of Osmotic and Crystalline Swelling, Hydrolisis, and Dehydration on the Ortho-Silicic Acid Structure of the Antimicrobial Cream:

In the present disclosure, clay provides silica ($SiO_3$), which is a silicic acid anhydride of monomeric ortho-silicic acid ($H_4SiO_4$), which is water soluble and stable in the presence of Blue Tartrazine, lauryl ether sulfate, and fatty acids. Moreover, several lower hydrated forms of ortho-silicic acid exist in aqueous solutions as well, including meta-silicic acid ($H_2SiO_3$) or lower oligomers, like di-silicic ($H_2Si_2O_5$) and tri-silicic acids ($H_2Si_3O_7$), including their hydrated forms, pentahydro-silicic ($H_{10}Si_2O_9$) and pyro-silicic acids ($H_6Si_2O_7$). The thermodynamic stability of the antimicrobial cream of the present disclosure may lead to the total bio-availability of silicon provided by the transfer or inorganic compounds through biological and organic compounds, which may have medical virtues and healing power.

Specifically, binary compounds may be formed between two elements, either a metal paired with a nonmetal or two nonmetals paired together. When a metal is paired with a nonmetal, they form ionic compounds in which one is a negatively charged ion and the other is positively charged. The net charge of the compound must then become neutral. In the present disclosure, there is the presence of 65% silicon, metalloproteins, organic anionic salt compounds (lauryl ether sulfate, Brilliant Blue, or Blue Tartrazine). Along with the Van der Waal bonds between the top silicate tetrahedral position, there may also be hydrogen bonds between inorganic and organic colloids, cations, and silicon. These hydrogen bonds may influence the silicate to react with the colloid and attach to a metal by a weak bond. Because of the structure of the quasi-regular $SiO_4$ tetrahedron, wherein the oxygens are attracted to the central silicon with a stronger binding strength than those of other cations, the crystalline structure results in the chemical formula $SiO_2$. Thus, some hydrous metal silicate compounds may be established, and the silicate structure may be hydrous sodium silicate, hydrous potassium silicate, or lithium silicate. These compounds may influence the arrangement of silicate in the composition, and these arrangements may be present due to the addition of talc within the kaolin clay material and the cracking process during synthesis. The presence of silicon in the cream is described in more detail below.

Mechanism of Crystalline and Osmotic Swelling in the Anti-Microbial Cream:

In the preset disclosure, and isomorphism substitution and a crystalline swelling may be observed, wherein crystalline swelling is a macroscopic energy balance model for crystalline swelling of 2:1 phyllosilicates. Crystalline swelling for a static system is modeled by a balance among the potential energies of attraction, repulsion, and resistance. The potential energy of attraction is due to both the electrostatic interaction between the interlayer cations and the negative surface charge sites and to Van der Waals attractions between layers. The potential energy of repulsion is due to the net hydration energy for the interlayer cations, the net hydration energy for the negative surface charge sites, and born repulsion. The potential energy of resistance is responsible for both hysteresis and the stepwise nature of crystalline swelling. Moreover, crystalline and osmotic swelling may be assisted due to the large amount of sodium chloride. Clay swelling is the result of d-spacing increase and volume increase whenever the exchangeable cations are hydrated. Crystalline swelling occurs in the presence of concentrated brines or brines that contain high concentration of divalent or multivalent cations. The formation of water layers on the surfaces of clay minerals causes crystalline swelling, with the concentrations below critical salt concentrations whereas osmotic swelling occurs when clay minerals are exposed to solutions that contain large quantities of sodium cations. Therefore, the regions for crystalline or osmotic swelling may be differentiated by the value of interplanar spacing. At critical salt concentrations, a discontinuity in the interplanar space may be observed. This is the transition point between crystalline and osmotic swelling. During osmotic swelling, binary compounds may be formed between two elements—either a metal paired with a nonmetal or two nonmetals paired together. When a metal is paired with a nonmetal, they form ionic compounds in which one is a negatively charged ion and the other is positively charged.

The formation of an electric double layer on the surfaces of the clay minerals cause clay swelling. In this case, more clay swelling and more formation damage would be expected.

Ortho-Silicic and Silicon Reactivity:

Hydrolysis and dehydration synthesis both deal with water and other molecules, but in very different ways. Both have a reverse reaction in relation to each other and vice versa. In the present disclosure, these processes involve the formation of polymers, ester, ester alkyl silanol, and ester di-alkyl silanol, which are linked together. The process may be accelerated during osmotic and crystalline swelling.

Moreover, with the presence of a stabilizer agent, ionic and hydrogen bonds may be created to increase the bioavailability of silicon. These compounds are formed when water is removed from a chemical equation and then monomers (small molecules) bond together. In order to break the bonds, water must be added. Thus, in the present disclosure, the following may occur: $(SiO_2)_n + 2H_2O \rightarrow (SiO_2)_{n-1} + Si(OH)_4$, wherein $n > 1$ and $SiO_2$ means solid silica or polysilicon acid in water.

Summary of the Chemical Changes During Synthesis:

The Kaolin clay has a chemical formula of $(Ca,Na,H)(Al, Mg,Fe,Zn)_2(Si,Al)(OH)_2 nH_2O$, wherein n is 2 or 3. The clay is treated with water and lauryl ether sulfate. As a result, the cations may relocate themselves in the interlamellar region and become exchangeable by a variety of both metallic and non-metallic ions (e.g., $H_3O^+$, $Al^{3+}$, $Fe^{3+}$), where this is shown below:

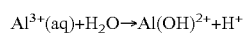

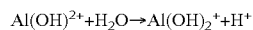

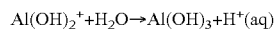

Thus, the following reactions take place:

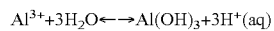

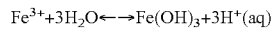

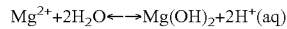

The presence of $H^+$ and $Cl^-$ results in the formation of HCl which causes, for example, the following:

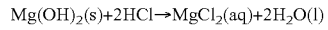

The presence of $Ca^{2+}$ and $OH^-$ results in the formation of $Ca(OH)_2$, which results in, for example, the following:

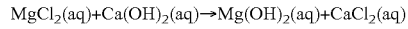

The presence of $Na^+$ and $Cl^-$ results in the formation of NaCl, which results in the following reactions:

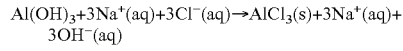

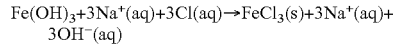

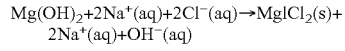

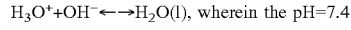

The above reactions may be activated with mechanical energy, and the formation of $FeCl_3$ may add a yellow coloring to the composition.

Brucite, which is a hydroxide of magnesium ($Mg(OH)_2$) is made up of octahedral magnesium hydroxide that stacks on top of one another. The overall charge of the molecule is zero.

Another basic structure is the structure of the gibbsite leaflets ($Al_2(OH)_6$), wherein the aluminum atoms replace the magnesium atoms. This results in a charge surplus because $Mg^+$ is replaced by $Al^{3+}$, resulting in dioctaedric and trioctaedric structures, which means that there are two or three cations, respectively, in the octahedral sites that occupy the aluminum and magnesium atoms in gibbsite and brucite. The negatively charged tetrahedral layers may be bonded by cation layers, such as $Mg^{2+}$ and $Al^{3+}$, which have a coordination of 6 and are thus located at quasi-regular octahedron centers. As a result, the tetrahedral layer is followed by an octahedral layer, and these two layers have the 4 oxygen atoms of the tetrahedral and the 2 oxyhydriles in common. The elementary mesh (a=0.52 nm, b=0.9 nn) contains size octahedral cavities, which occupy bivalent ions, such as $Mg^{2+}$. Under these conditions, the layer is called trioctahedral. At the same time, two thirds of these cavities are occupied by trivalent ions, such as $Al^{3+}$, and the layer is called dioctahedral.

Galenic Structure of the Antimicrobial Cream

The antimicrobial cream of the present disclosure may have a galenic structure. To establish the galenic structure of the antimicrobial cream, the behavior of silica, starting from the synthesis of the antimicrobial cream, until the formation of ortho-silicic acid in the presence of sodium chloride, lauryl ether sulfate, and Blue Tartrazine may be beneficial to understand.

The reaction begins as follows:

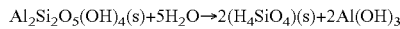

$$Al_2Si_2O_5(OH)_4(s) + 5H_2O \rightarrow 2(H_4SiO_4)(s) + 2Al(OH)_3$$

This reaction represents the transformation of a mineral compound to an organic compound. The presence of organic silicon is provided by the presence of large sufficient amounts of sodium chloride, lauryl ether sulfate, Blue Tartrazine, vitamins, gelatin, and fatty acids. During this process, there is observation of the gradual solubility of silicon, which is generated by alkylation, dialkylation, hydrolyzation, dehydration, condensation, chelation, and cation exchange. The solubility of silica in water is a basic factor in the behavior of silicic acid. Specifically, when sold phases of silica are in contact with water, small amounts of silica dissolve and enter the aqueous phase. The dissolution and deposition of silica in water involves both hydration and dehydration reactions. Additional compounds may be formed by chelation of silicon ($Si^{4+}$ and $Al^{3+}$) or cation exchange by Blue Tartrazine or brilliant blue and lauryl ether sulfate. These compounds are the organic silicon salts, which provide strong biological stability and the ability to begin the skin disease and wound healing processes.

Criteria for the Microscopic Structure of Clays

Important criteria of the clays are position, nature and degree of substitution, position, and nature of the interlayer load and the relocation of the load throughout the layer. A swelling occurs in the interlayer space as a result of the presence of water, lauryl ether sulfate, and mechanical energy in the antimicrobial product. Specifically, two swellings may occur: (1) a crystalline swelling; and (2) an osmotic swelling after and during the mixing using mechanical energy. For the other cations, meaning all other cation oxides other than the oxide cations of $Al^{3+}$ and $Si^{4+}$, only the crystalline swelling is observed.

As a result, the following trends are observed. The moisture content tends to reduce the dry unit weight, because water lauryl ether sulfate, and fatty acids take up the space that would have occupied the water particles. The component (water, lauryl ether sulfate, fatty acid) at which the maximum dry unit weight is attained forms the antimicrobial cream of the present disclosure. As isomorphic substitution, which is the replacement of one atom by another of similar size, may assist the above phenomena without disrupting the crystal structure of the embodiments. For example, iron oxides can be easily substituted by cations of neighboring ionic radii, such as Al, Mn, Cu, and Ti, without modifying the structure and, thus, while developing little permanent change. Fe(III) is present in hematite, goethite, or ferruhidride crystalline forms and in an amount of about 46% by mass. However, other cations ($Mn^{2+}$, $Zn^{2+}$, $Cu^+$, $Cu^{2+}$, $Mg^{2+}$, $Ti^{4+}$, $Al^{3+}$, and $Mo^+$) may be incorporated into the structure of the oxide.

Iron oxides, which are finely divided minerals have a size of from about 10 to 100 amstrong (a), may be the main source of metal. In comparison, aluminum oxides are very unaffected by $Al^{3+}$ substitutions and are large in size. Thus, they do not develop permanent loads and little variable load. The oxides of iron and aluminum are positively charged and exhibit strong pHzpc, wherein pHzpc is the pH of zero point of charge and corresponds to the pH value at which the surface of the solid is considered to be neutral Manganese oxides are scarce in the composition of the present disclosure and are very complex from a mineralogical point of view. They have a more diverse octahedral arrangement and composition than iron and aluminum oxides with, for example, octahedral layers containing aluminum and lithium, layered structures or tunnels that contain large cations ($K^+$), and the capacity to exchange cations to fix various metallic trace elements (Cu, Zn, Ni) having pHzpc values around 5 to 7. The fixation of metals can exceed the exchange capacity of the manganese oxide by incorporating metal, such as cobalt, into the crystal lattice.

In the composition of the present disclosure, the minerals are subject to substitutions for two reasons: (1) the presence of Brilliant blue and lauryl ether sulfate; and (2) coprecipitation of ions of the lower valences within the crystalline mesh ($Al^{3+}/Fe^{2+}$ or $Mg^{2+}Si^{4+}$, $Al^{3+}$), which allows the ions to develop a permanent load. The inorganic colloid surface charge may thus be permanent (isomorphic substitution). The inorganic colloids container in the antimicrobial cream of the present disclosure may thus participate in specific or non-specific absorption reactions allowing the fixing of cations.

The participation in the absorption reaction may be varied by the functional ionization of surfaces or ion absorption, degrees of solubility of iron oxides containing antimicrobial cream under crystallinity conditions, and their formation conditions in the Kaolin phase.

The compounds may be distinguished as gibbsite ($Al(OH)_3$), goethie (FeOOH), hematite ($FeO_3$), and poorly crystallized compounds (AlOOH, BOCHNITE). The antimicrobial cream of the present disclosure may possess permanent changes, however, in the SiOH and AlOH groups, wherein the angles of the associated crystals release additional negative charges ($SiO^-$, $AlO^-$). ($AlSiO_4)^-$ and ($SiO_2$) may also be present and may provide stability in a biological environment.

Isomorphic substitution may occur in the tetrahedral layers ($Si^{4+} \rightarrow Al^{3+}$, $Fe^{3+}$) or in the octahedral layers ($Al^{3+} \rightarrow Mg^{2+}Fe^{2+}$ or $Mg^{2+} \rightarrow Li^{2+}$). The substitutions may result in a load deficit, which may be expensed outside the loads.

When fatty acids, water, lauryl ether sulfate, and gelatin are added to the composition, they act as softening agents on the clay particles and move into a densely packed position, which requires mechanical energy. The interlayer boding between the tops of the silica layers is mainly due to Van der Waals attractions and other ion bonding, such as: interlayer position ($Na^+$, $Ca^{2+}$, $H_3O^+$); tetrahedral (Al, Si); and octahedral ($Al^{3+}$, $Fe^{2+}$, $Fe^{3+}$, $Cu^+$, $Cu^{2+}$, $Mg^{2+}$, $Zn^{2+}$, $Mn^{2+}$, $Mo^+$, $Ti^{4+}$). Thus, the bonding strength is weak, along with being softened by the water, lauryl ether sulfate, and fatty acid.

Therefore, the amount exchangeable ions from of water, lauryl ether sulfate, and fatty acids may be easily separated. The water, fatty acids, and lauryl ether sulfate may swell the clay because of the affinity for water. As a result, the cream may be susceptible to substantial volume change as a result of the swelling. The swelling may be caused by water gaining entry into the lattice structure, which may then shrink if the water, lauryl ether sulfate, or fatty acids are removed. The total energy between the particles may decrease as they approach each other.

Throughout the present disclosure, the notation (Na, Ca) means that Na and Ca are present in the same crystal sites in varying proportions. Simultaneous (Si, Al) replacement ensures that the elements remain in their normal oxidation states. However, even the formulas disclosed herein are approximate, as several other elements may be present.

In the antimicrobial cream of the present disclosure, the position of the exchangeable cations is not able to be determined precisely, because they can pass from one host site (hexagonal site) to another depending on the relative humidity, lauryl ether sulfate, fatty acids, and energy conditions to which they are subjected. The notion of host sites makes sense only as long as the cation remains bound to the clay surface. The movement of the cations may be followed by measurements of electrical conductivity. When the cations are hydrated, the layers may be sufficiently spread apart to allow the cations to pass from one site to another, and an electric current may be measured. The current may be a function of the compensating cation and the interactions between the clay surface and the cation. However, there may also be an electric current that generally remains ascribed to the compensating cations, although generally the clay of the present disclosure is described as frozen for the dry state.

Use of the Product for Skin Regeneration:

In the regeneration process of skin, calcium may be very important. Calcium has an established role in the homeostasis of mammalian skin and serves as a modulator in Keratinocyte proliferation and differentiation. Gradients of calcium concentrations increasing from 0.6 mM in the basal layer to >1.4 mM in the stratum *granulosum* are consistent with migration patterns in response to minor abrasions (normal wear). Dermal fibroblasts require calcium, but are approximately 100 times less sensitive than Keratinocytes. Normal calcium metabolism in the skin is dependent on cell membrane and cytosolic calcium binding proteins (calmodulin, cadherins, etc.). In wound repair, calcium is predominantly involved as Factor IV in the hemostatic phase, but it is expected to be required in epidermal cell migration and regeneration in later stage healing. Calcium is a potential central regular in wound healing. Also, a sustained elevated intracellular calcium ($Ca^{2+}$) concentration has thus emerged as a universal and require characteristic of activated cells. Activation of stem cells by $Ca^{2+}$ was accomplished by the use of the antimicrobial green clay cream of the present disclosure.

In the antimicrobial cream of the present disclosure, the role of $Ca^{2+}$ in stem cell activation suggests that the cells use the intracellular $Ca^{2+}$ concentration as a gauge to respond dynamically to the multitude of signals vying for their attention. Stem cells may adjust their proliferation activity in response to a wider variety of $Ca^{2+}$ signals. Thus, the extra concentration of calcium may emerge as a master regulator of stem cell activity. In other words, the $Ca^{2+}$ level in the antimicrobial cream may regulate stem cell activity (such as L-glutamate activity) by triggering a sustained increase of $Ca^{2+}$ within the cell. It should be noted that this change is not limited to the response to L-glutamate.

In the process of healing a wound or burn with the antimicrobial cream, the cells may acquire the molecules and ions needed from the area surrounding the cells. Thus, there may be an increased traffic of molecules and ions in and out of the cells through their plasma membrane. In healing wounds and skin regeneration, two problems should be considered:

Relative concentrations of molecules and ions, and ions moving spontaneously down their concentration gradient diffusion (1) Lipid layers are impermeable to most essential molecules and ions. The bilayers are permeable to water molecules and few other small, uncharged molecules, like oxygen ($O_2$) and carbon dioxide ($CO_2$, which may diffuse into or out of the cells through the plasma membrane in a process referred to as osmosis. However, lipid bilayers are impermeable to $K^+$, $Na^+$, $Ca^{2+}$, $Cl^-$, and $HCO_3$.

Small hydrophilic molecules, such as glucose, and molecules, like proteins and RNA, can be transported into cells by the facilitation of ligand transmembrane proteins. For example, the direct active transport with $Na^+/K^+$ ATPase is established by the active transport of both ions. Specifically, cytosol in human cells contains a concentration of potassium ions ($K^+$) that is as much as 20 times higher than in the extracellular fluid, and the extracellular fluid contains a concentration of $Na^+$ as much as 10 times greater than within the cell. By the known sodium potassium pump mechanism, three $Na^+$ ions are actively transported out of the cell for every 2 $K^+$ ions pumped into the cell. This process helps establish a net charge across the plasma membrane with the interior of the cell being negatively charged with respect to the exterior. The resting potential may prepare nerve and muscle cells for the propagation of action potentials leading to nerve impulse and muscle action.

Normally, accumulation of sodium ions outside of the cells draws out the cells ability to maintain osmotic balance, wherein the gradient of sodium ions is harnessed to provide the energy to run several types of indirect pumps. The importance of the roles of $Na^+/K^+$ ATP may be reflected in the fact that almost ⅓ of all energy from mitochondria in human cells is used to pump. In the healing process, the antimicrobial cream of the present disclosure may help human cells regulate osmosis balance by the presence of both Brilliant Blue and sodium laureth sulfate, while also assuring stability by the balance of $Na^+$ ions in fixing the $Ca^{2+}$ ions. $Zn^{2+}$, $Fe^{2+}$, $Fe^{3+}$, and $Al^{3+}$ may act as pumps, attracting $Na^+$ and providing the necessary ions for regeneration of damaged cells to wounds, burns, infections, and the like, while ensuring harmony and normal cellular function.

$Ca^{2+}$/ATPase:

$Ca^{2+}$/ATPase is located in the plasma membrane of all eukaryotic cells, which use the energy provided by one molecule of ATP to pump $Ca^{2+}$ ions in and out of the cell. This activity helps to maintain concentration gradients between the cytosol and outside of the cell. During the process of healing rounds and burns, all elements, vitamins, and minerals, including $Ca^{2+}$ may be beneficial to regenerate cells. In the green antimicrobial cream of the present disclosure, calcium is present, as evidenced by the chemical structure of the final product.

The Role of Silicon Contained in the Green Clay Cream:

Silicon may allow molecular structures to be established and the metabolism to function. Specifically, silicon may be necessary for the synthesis of collagen, elastin, and hyaluronic acid. Thus, silicon may influence the formation of connective tissue, including cartilage, bone, and skin, and may improve a body's immunity. The silicon may initiate the growth and regeneration of cells and body structures. In elastin and collagen, silicon may protect the vascular wall, veins, and arteries. With respect to the skin, the silicon may act as the dermis that the epidermis finds itself attached to. The present disclosure justifies the passage from a mineral product to an organic product with high reactivity of the ortho-silicic acid. Organic silicon and ortho-silicic acid induce or regulate the multiplication of fibroblasts, which are responsible for the formation of collagen and elastin, thus managing flexibility and elasticity. Organic silicon or ortho-silicic is found in various organ and glands, such as the lungs, spleen, liver, heart, brain, pancreas, adrenals, skin nail, and hair, and stimulates immune functions by promoting the multiplication of lymphocytes and increases the secretions of antibodies by plasma cells. The ortho-silicic acid and silicon potentiates the action of zinc, cooper, and iron that (i) are involved in biochemical reactions of the organism; (ii) control, activate, and regulate the metabolism of cell, (iii) bound or influence oligo-element, metalloproteins, enzymes, vitamins, and assimilates minerals (calcium, magnesium, potassium) and other beneficial substances (flavonoids, vitamin C, quercetin) to perform cellular metabolism, in the process of wound healing, burns, and skin disease therapy. Also, ortho-silicic acid has an anti-inflammatory action and potentiates the activity of iron, copper, zinc, selenium, and the functioning effect of the mitochondria. Organic silicon and ortho-silicic increase the activity of adenyl cyclase used to manufacture ATP by mitochondria. The artho-silicic role in many other biochemical reactions involve key enzyme such as: proline, hydroxylase, ornithine, aminotransferase. The Dehydroepiandrosterone (DHE) is manufactured in mitochondria, and its production decreases with age in parallel with the fall of silicon. Obviously, there are similarities between DHEA and organic silicon. Supplementations with Omega-3, Vitamin D, Iron, antioxidant of vitamin E type, Co-enzyme Q-10, alpha lipoid acid may be necessary to compensate the falling effect of organic silicon and ortho-silicic acid.

Silicon may also play a role when it comes to the immune system and hormones. As mentioned above, silicon may be essential for formation of the skin, joints, nails, and hair and, thus, its presence may improve healing, which improves the immune system, maintains flexibility, and strengthens blood vessels. Silicon's presence may also prevent aging and inflammation. Silicon may also help with electrical connections in the brain and other areas of the body. Because silicon is such a prevalent and beneficial element, the green cream clay that contains silicon may help regenerate skin in wounds, burns, and ulcers.

Moreover, silicon is tetravalent, meaning it may be able to create hydrogen bonds with nitrogen and oxygen in wounds, allowing it to react with molecules containing these two elements. The organic silicon ortho-silicic acid may thus consolidate the structure or promote the enzymatic catalysis of certain molecules, such as collagen, elastin, phospholipids, and structural proteins, such as hyaluronic acid and glucosamine.

The skin cream of the present disclosure may, therefore, comprise an antimicrobial, kaolinite and montmorillonite green cream clay composition with weak acids (fatty acids), oleic acids, benzoic acids, clove oil (C5, C14 antimicrobial properties and anti-aging abilities and properties), trace elements, vitamins, and mineral elements. The final skin cream may provide the ability and function of healing skin disease, Buruli ulcers, wounds, and burns without spots or scars. In some embodiments, the cream may be used with poultice and compresses for burns and deep wounds.

Antimicrobial Abilities of the Cream of the Present Disclosure

The Kaolinite structure unit includes alternating layers of tetrahedral silica with tips embedded in an alumina (gibbisite) octahedral unit. The chemical formula may be $Al_2(Si_2O_5)(OH)_4$. Common mineral elements that may be present include Fe, Mg, Na, K, Ti, Ca, and $H_2O$. The gelatin may contain Zn, Cu, and Ca. The water may contain Mg, Na, Ca, Fe, Zn, Cu, K, and Mn.

As described above, the composition may also include talc ($H_2Mg_2(SiO_3)$ or $Mg_3SiO_{10}(OH)_2$, wherein the talc may include Mg, Mn, Ti, Fe, and Ca and, thus, the talc may be the source of magnesium and silicon. Talc is a mineral that develops during chemical reactions produced by the circulation of hydrothermal fluids rich in silica in magnesium rocks. The minerals most commonly associated with talc are chlorites. Other associated minerals are tremolite, serpentine, snthophyllite, actinote, magnesite, dolomite, and chromite.

Lauryl ether sulfate and Brilliant Blue or Blue Tartrazine may be beneficial in the process of wound healing, and they may have antimicrobial properties. Specifically, these molecules may provide for polystyrene cation exchange. Sodium polystyrene effects the exchange of sodium and potassium in the body. Sodium polystyrene sulfonate may be used to treat high levels of potassium in the blood, also called hyperkalemia. In the cream of the present disclosure, the ions present in the product may exchange the cations necessary for skin regeneration, wound healing, and treating skin infections by creating an antimicrobial compound (zin coceth sulfate, magnesium coceth sulfate) and introducing the ions necessary to reactivate and regenerate damaged cells in the wound or infection.

The presence of lauryl ether sulfate, talc, and gelatin causes the composition to acquire a montmorillonite structure and function, wherein the structure comprises two silica layers and one alumina layer, wherein the alumina octahedral layer is sandwiched between two silica layers with tetrahedral tips. The interlayer bonding between the tops of the silica layers is mainly due to Van der Waals forces and, thus, has the composition may include a high presence of hydrogen or other ion bonding, such as $Na^+$, $Ca^{2+}$, $K^+$, $Mg^{2+}$, $Zn^{2+}$, $Al^{3+}$, $Fe^{2+}$, $Fe^{3+}$, $Cu^+$, $Cu^{2+}$, and $Ti^{4+}$.

Hard metal and heavy metal ions ($Ca^{2+}$, $Zn^{2+}$, $Mg^{2+}$, $Fe^{3+}$, $Fe^{2+}$, $Al^{3+}$, and the like) are contained in the cream of the present disclosure. Sodium ($Na^+$) may be considered a weak or soft metal ion and is contained in the lauryl ether sulfate and Brilliant Blue or Blue Tartrazine. Like polystyrene sulfonate, lauryl ether may exchange its sodium ion and capture a heavy metal contained in the gray clay during the synthesis process, acquiring the antimicrobial properties described above. An exemplary compound that may be formed during the synthesis of the cream of the present disclosure is zinc coceth sulfate, the structure of which is shown below:

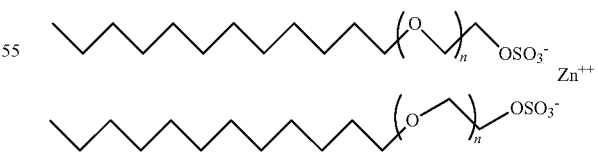

Zinc coceth sulfate may be obtained by cation exchange including the migration of a heavy metal into polystyrene sulfonate, wherein the weak ion (sodium in the sodium ether lauryl sulfate) may be displaced by the polystyrene sulfonate and captured by the zinc ions contained in the clay.

Zinc coceth sulfate may be useful for treating skin disorders associated with *Propionibacterium acnes*.

The synthesis of zinc coceth sulfate is shown below:

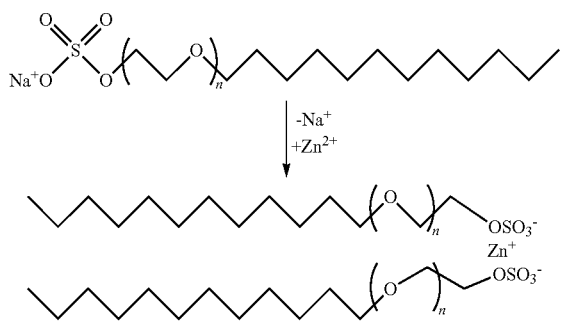

Another exemplary compound that may be formed is magnesium (Mg$^{2+}$) coceth sulfate, the structure of which is shown below:

Magnesium coceth sulfate has antimicrobial properties and may be important in the treatment of skin infections, particularly when a person has a large wound or poor skin restoration abilities due to diabetes, psoriasis, leprosy, and Buruli Ulcers. The magnesium binds calcium and is involved in calcium metabolism on the parathyroid glands. At the cellular level, it controls and regulates the entry of calcium into the cell and intracellular fluids.

Magnesium may inhibit cation channels, such as sodium and calcium receptors, and may act as a calcium antagonist. It may thus protect mitochondria against calcium overload. In the wound healing process, magnesium may play primarily an intracellular role. Also, formed is MgCl$_2$. The MgCl$_2$ present in the composition of the present disclosure may allow damaged cells to regain their phagocytic power in a large proportion.

Polystyrene Exchange Process

The exchange process may be performed by lauryl ether sulfate and brilliant blue, which may act as pump membranes with the ability to displace soft or weak metals by fixing hard metals in the damaged cells, wherein the hard metals may help with cell regeneration. They may also act as a barrier between the heavy metal and the sodium ion by establishing the barrier and controlling the flux of ions (mainly sodium) in the body. The barrier may help to fix ions (Ca$^{2+}$, Mg$^{2+}$, Mn$^{2+}$, Fe$^{2+}$, and Fe$^{3+}$) in the human body with the purpose of wound healing and treating skin infections. Moreover, they may act as a regulator of osmosis activity between extra and intra cells by maintaining flux of important mineral elements through damaged cells (wounds, burns, skin infections, etc.). They may additionally act to rehabilitate skin minerals in the case of alopecia treatment, and to rejuvenate the skin and help prevent or combat wrinkles, and, finally, to prevent sodium ions from penetrating into cells and manage osmotic pressure between the intra and extra cellular environment, balancing the pressure within the cells.

In the composition of the present disclosure, the polystyrene exchanges the heavy metal by displacing Na$^+$, creating more antimicrobial compounds, which may be helpful in healing wounds and skin infections. Many new compounds may be formed by the exchange of sodium ions. The compounds also include calcium coceth sulfate, magnesium coceth sulfate, zinc coceth sulfate, iron coceth sulfate, potassium coceth sulfate, and the like. The structures of these compounds are shown below:

Calcium (Ca$^{2+}$) coceth sulfate:

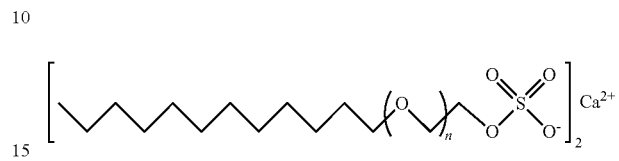

Magnesium (Mg$^{2+}$) coceth sulfate:

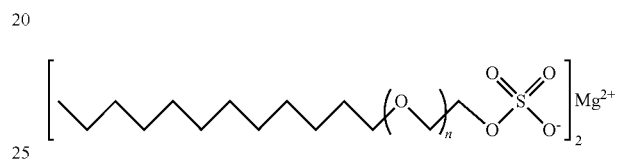

Zinc (Zn$^{2+}$) coceth sulfate:

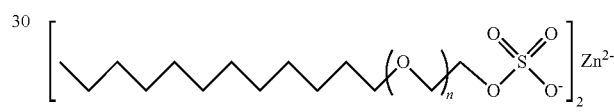

Iron (ii) (Fe$^{2+}$) coceth sulfate:

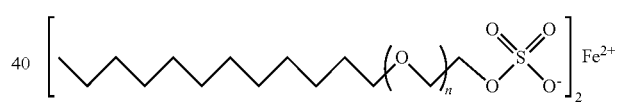

Iron (iii) (Fe$^{3+}$) coceth sulfate:

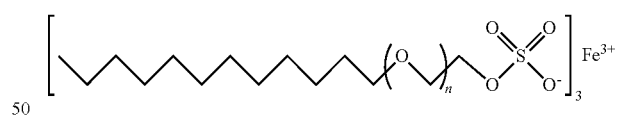

Potassium (2K$^+$) coceth sulfate:

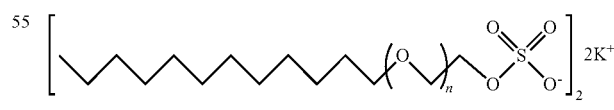

Aluminum (Al$^{3+}$) coceth sulfate:

Manganese (Mn$^{2+}$) coceth sulfate:

Copper (ii) (Cu$^{2+}$) coceth sulfate:

Copper (i) (Cu$^+$) coceth sulfate:

Titanium (Ti$^{4+}$) coceth sulfate:

Molybdenum (Mo$^+$) coceth sulfate:

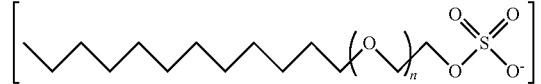

The exchange processes are outlined below, wherein Brilliant Blue or Blue Tartrazine is the polystyrene sulfonate.

The antimicrobial compound may also include Ca$^{2+}$ ions as a result of calcium chloride. Ca$^{2+}$ intracellular processes may enhance wound healing and skin disease therapy:

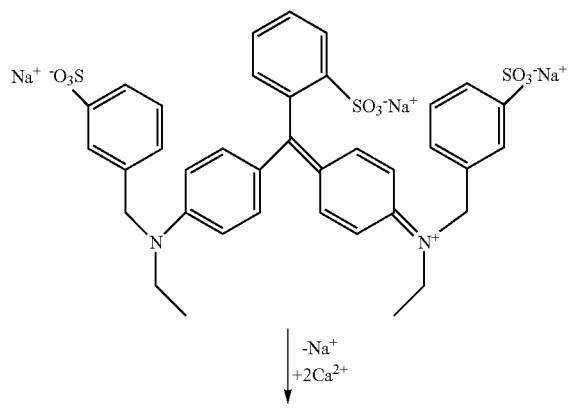

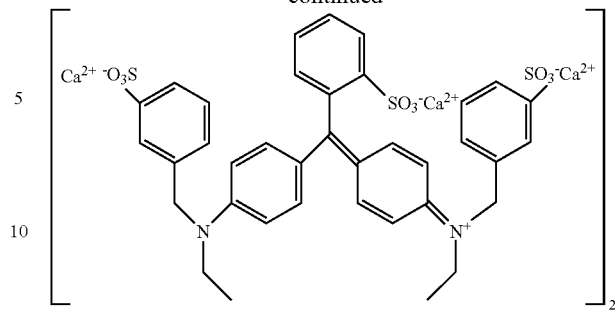

The antimicrobial compound may include magnesium via a reaction with magnesium chloride, wherein Mg$^{2+}$ may improve wound healing and skin disease therapy.

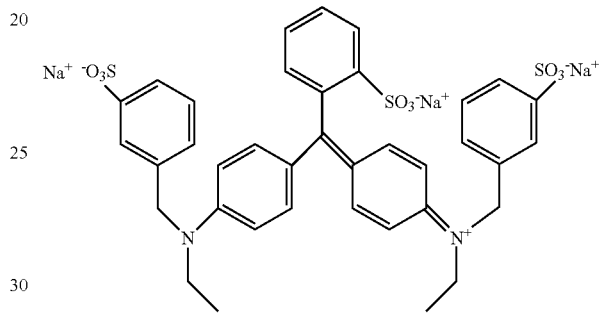

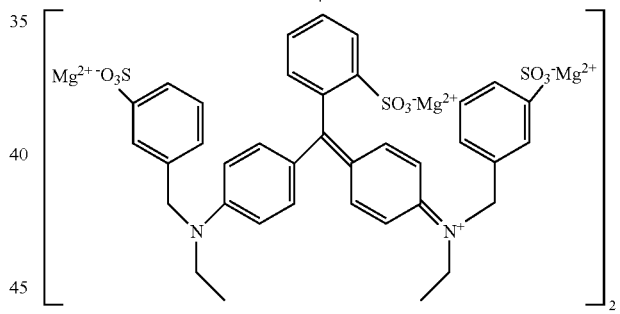

The antimicrobial compound may include zinc ions, wherein Zn$^{2+}$ may improve intracellular processes involved in wound healing and skin disease therapy. In the cream of the present disclosure, zinc plays an important role in the structure of proteins and cell membranes. A finger-like structure, known as a zinc finger motif, stabilizes the proteins. Copper provides the catalytic activity for the antioxidants enzyme, copper zinc superoxide dismutase (CuZn-SOD). Zinc proteins regulate gene expression by acting as transcription factors binding to DNA and influencing the transcription of specific genes.

Zinc also plays a role in cell signaling to influence hormone release and nerve impulse transmission. Zinc plays a role in apoptosis, a critical cellular regulatory process with implication for growing and development. Zinc is also an essential trace mineral for DNA synthesis, cell division, collagen formation, protein synthesis, and immune function, which are all necessary processes for tissue regeneration and wound repair. Zinc is also necessary to develop and activate T-lymphocytes, which are important to the immune system.

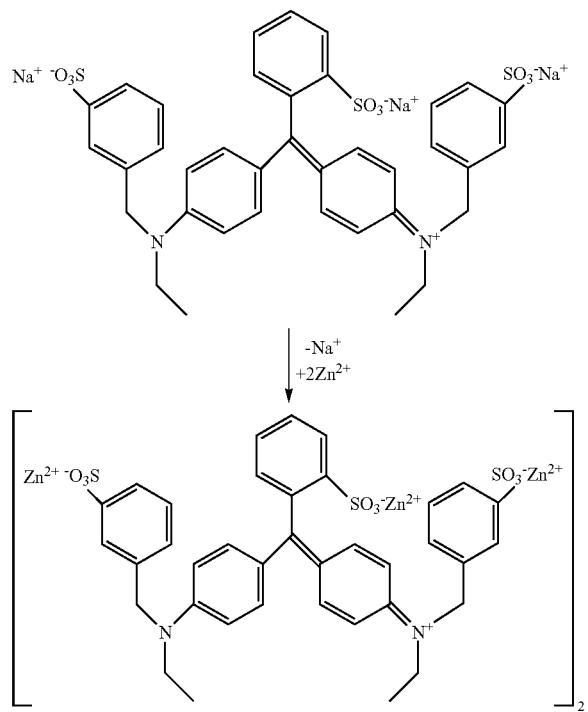

The antimicrobial compound with iron (II) may improve intracellular processes involved in wound healing and skin disease therapy, because iron may play a key role in both oxidative stress and photo-induced skin damage. Iron may be considered a vital co-factor for proteins and enzymes involved in energy metabolism respiration DNA synthesis. Iron may have a specific function, such as the metabolism of collagen by procollagen-proline dioxygenase.

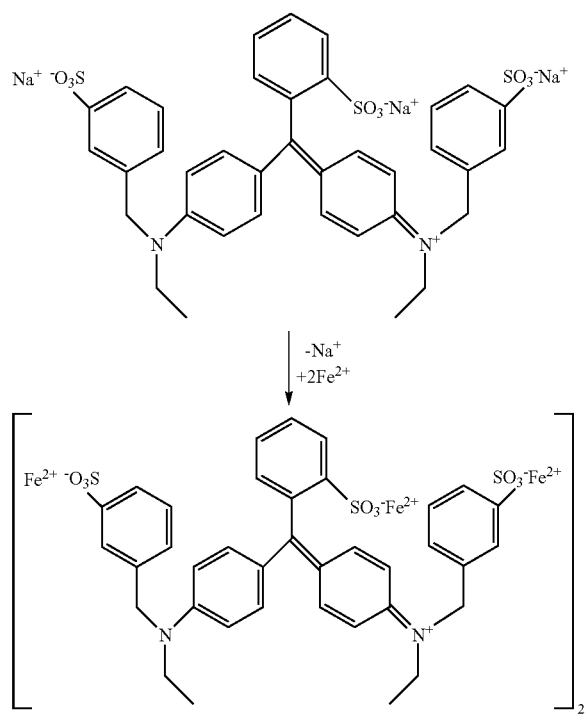

The antimicrobial compound may include iron (III) ions, which may improve intracellular processes involved in wound healing and skin disease therapy, wherein iron is a transition metal that may exist in two stages: $Fe^{2+}$ and $Fe^{3+}$. Intracellular labile may undergo redox cycling between its two most stable oxidations states and react as a superoxide anion with hydrogen peroxide giving hydroxyl radicals. In this process, iron (II) and iron (III) may be used to transport oxygen or catalyze electron transfer reactions, nitrogen fixation, or DNA synthesis.

Four copper containing enzymes, known as multi-copper oxidase (MCO) or ferroxidases, have the capacity to oxidase ferrous iron ($Fe^{2+}$) to ferric iron ($Fe^{3+}$), which is the form of iron that may be loaded onto the protein transferrin for transport to the site of red blood cell formation. The MCO family comprises the circulating cerruplasmin, the membrane bound cerruplasmin, and two proteins. The cuproenzyme, tyrosinase, is required for formation of the pigment melanin, which is formed into cells called melanocytes and plays a role in the pigmentations of hair, skin, and eyes. The cerruplasmin may function as an antioxidant in two different ways. Free copper and iron ions are powerful catalysts of free radical damage. By binding copper, cerruplasmin prevents free copper ions from catalyzing oxidative damage.

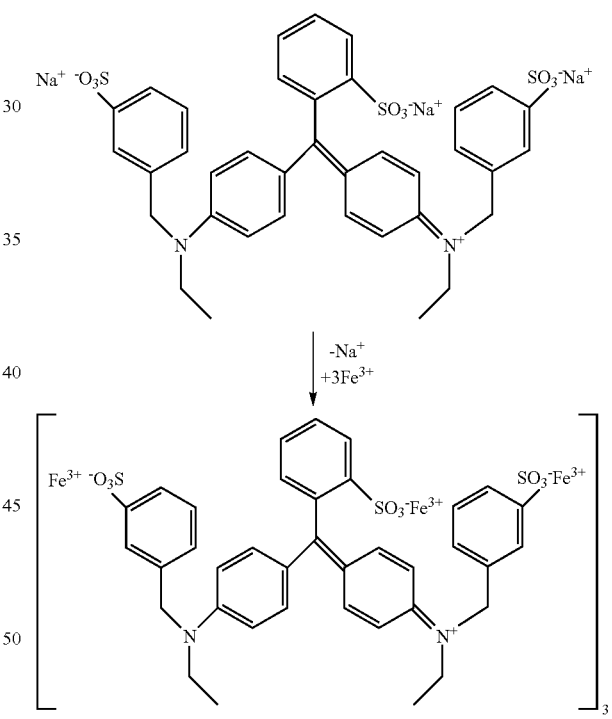

The antimicrobial compound may include potassium ions, wherein $K^+$ may improve intracellular processes involved in wound healing and skin disease therapy. In the present disclosure, the sodium does not penetrate the cells because of two barriers—the heavy metal with the pump polystyrene sulfonate and $Na^+/K^+$ ATP. Actively, there are 3 $Na^+$ transported out of the cell for every 2 $K^+$ pumped into the cell. This process helps establish a net charge across the plasma membrane with the interior being negatively charged with respect to the exterior.

Moreover, potassium is the principal positively charged ion (cation) in the fluid inside the cells, while the sodium is the principal cation in the fluid outside the cells. Potassium concentrations are about 30 times higher inside than outside cells, while sodium concentrations are more than 10 times lower inside than outside cells. The concentration difference between potassium and sodium across the cell membrane may create an electrochemical gradient known as the membrane potential.

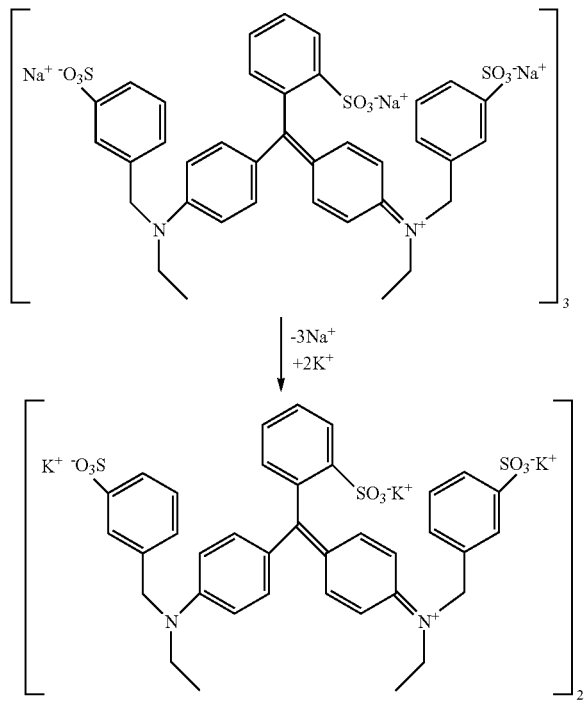

The antimicrobial compound may also include $Al^{3+}$ ions, wherein there may be a correlation between silicon and aluminum ions. Silicon and aluminum $[AlSiO_4]^-$, $(SiO_2)$ may provide stability in a biological environment. Silica may increase the anti-inflammatory capabilities under the control of aluminum. In the wound healing process, silicon may extract abnormal aluminum proteins in damaged cells and, thus, help accelerate skin regeneration. In the composition of the present disclosure, aluminum together with silicon may help initiate and regularize the immune system in wounds, burns, and skin lesions. Silicon may reduce or regulate the multiplication of fibroblasts in the healing process of wounds, burns, lesions, and skin regeneration.

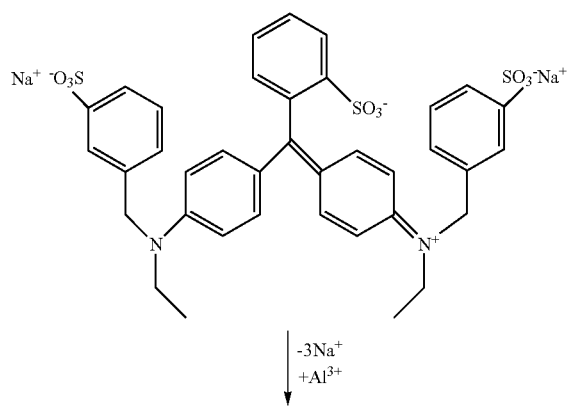

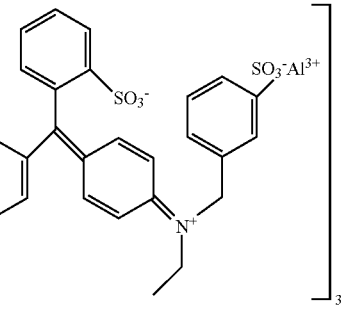

The antimicrobial compound may also include $Cu^{2+}$ ions, wherein the intracellular processes may enhance wound healing and skin disease therapy. Copper plays a key role in angiogenesis and in the expression and stabilization of extracellular skin proteins. Copper may also be an essential cofactor for oxidation-reduction reactions involving copper containing oxidases. Copper enzymes regulate various physiologic pathways, such as energy production, iron metabolism, connective tissue maturation, and neurotransmission. Thus, copper may be considered an essential trace element for humans and animals. In the body, copper shifts between the cuprous ($Cu^{2+}$) and cupric ($Cu^+$) forms; although, the majority of the body's copper is in the cuprous form.

The copper dependent enzyme, cytochrome c oxidase, plays an important role in cellular energy production. By catalyzing the reduction of molecular oxygen to water, cytochrome c oxidase creates an electrical gradient used by the mitochondria to create ATP. Another cuproenzyme, lysil oxidase, is required for the cross-linking of collagen and elastin, which may be important for the formation of strong and flexible connective tissues, which helps maintain the integrity of connective tissue in the heart and also plays a role in bone formation.

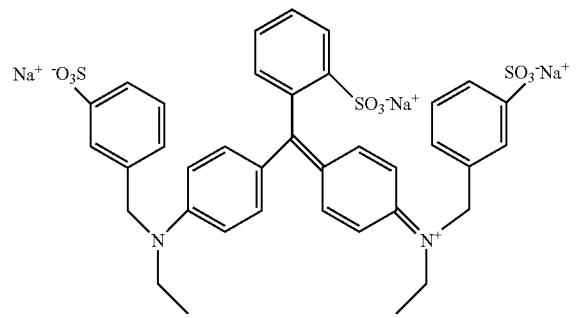

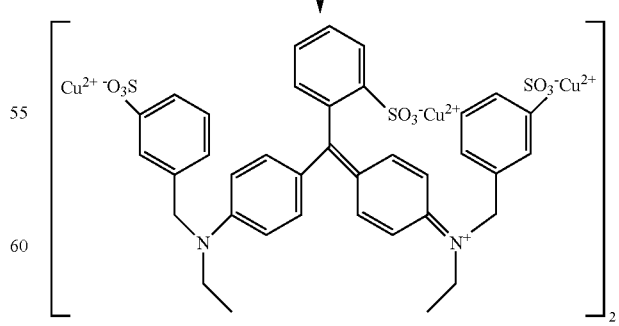

The antimicrobial compound may also include $C^+$ ions, wherein the intracellular processes may enhance wound healing and skin disease therapy:

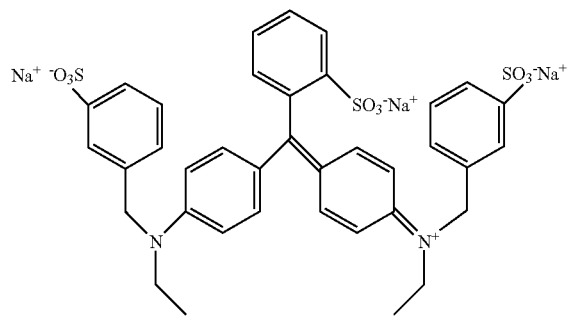

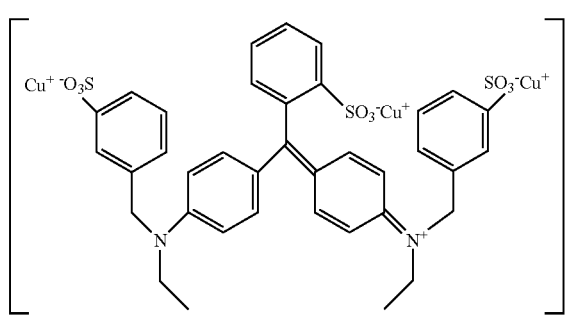

The antimicrobial compound may also include $Mn^{2+}$ ions, wherein the intracellular processes may enhance wound healing and skin disease therapy. Wound healing is a complex process that requires increased production of collagen. The manganese in the cream of the present disclosure may activate prolidase, which is an enzyme that functions to provide the amino acid, proline, for collagen formation in human skin cells. Glycosaminoglycan synthesis, which requires manganese-activated glycosyltransferases, may also be important in wound healing.

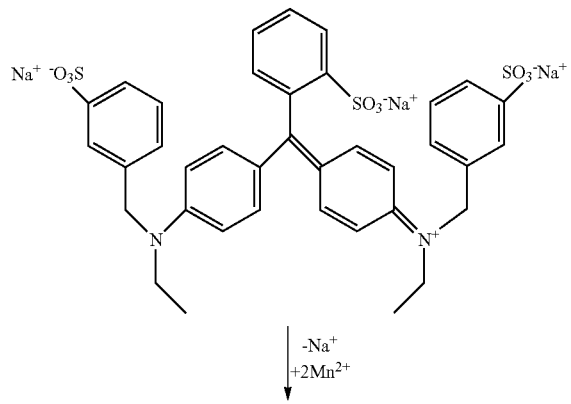

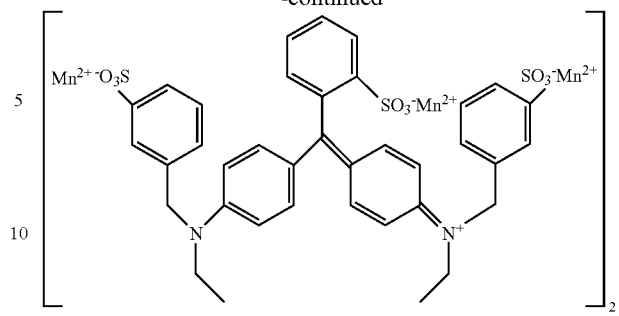

The antimicrobial compound may also include $Ti^{4+}$ ions, wherein the intracellular processes may enhance wound healing and skin disease therapy:

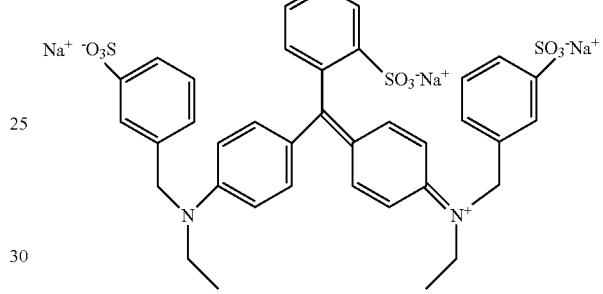

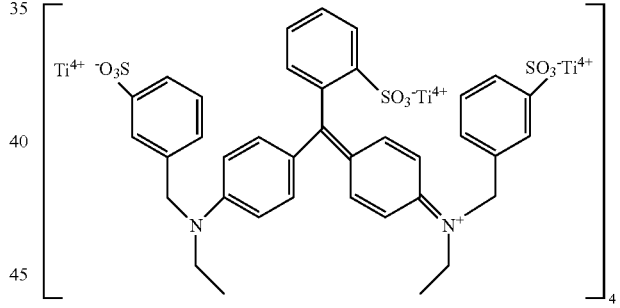

The antimicrobial compound may also include $Mo^+$ ions, wherein the intracellular processes may enhance wound healing and skin disease therapy. Molybdenum is a trace element that may be beneficial in the activation of various chemical reactions and to eliminate certain products synthesized during the digestion of the proteins. It also participates in the metabolism of fatty substances. Molybdenum may be essential for the metabolism of taurine, and it may intervene in the metabolism of sulfur and in the needs to copper. Molybdenum is an antagonist of copper. In the case of a molybdenum deficiency, there may be an intolerance to sulfur amino acids: cysteine and methionine. A deficiency in molybdenum may hinder the metabolism of the nitrogen from which a possible chlorosis forms (a form of anemia with the greenish huge of the skin). Molybdenum may catalyze xanthine oxidase to bind iron to ferritin. Anti-anemia may be a vital property of the enzyme responsible for the use of iron. It promotes the intestinal absorption of the iron as well as its destocking within the organism.

Specifically, ferroxidase activity of ceruloplasmin may facilitate iron binding into its transport protein, transferrin, and may prevent free ferrous ions from participating in harmful free radical generating reactions. The regulation of gene expression cellular copper levels may affect the synthesis of protein by enhancing or inhibiting the transcripts of specific genes. Copper may regulate the expressions by increasing the level of intracellular oxidative stress. Finally, adequate copper amounts in the body may be necessary for normal iron metabolism and blood cell formation.

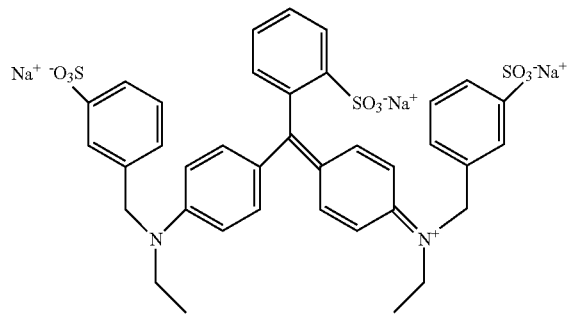

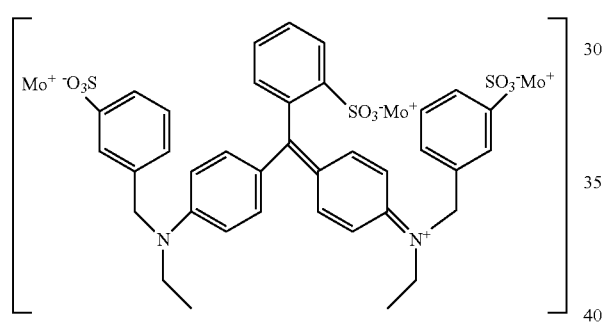

When it comes to magnesium coceth sulfate, magnesium chloride may activate the phagocytic leukocyte. Thus, magnesium chloride in the cream of the present disclosure may allow damaged cells to regain their phagocytic power in a proportion of about 300%. Thus, the magnesium chloride may help with the wound healing process.

The antimicrobial cream of the present disclosure may be synthesized using either Blue Tartrazine or brilliant blue. The reactivity of Blue Tartrazine is shown below.

The biological and organic compound of Blue Tartrazine in the antimicrobial cream is:

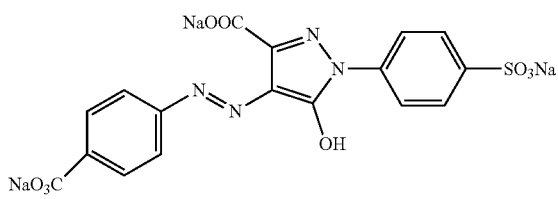

When Blue Tartrazine reacts with $Si^{4+}$ in the antimicrobial composition, the following may be formed:

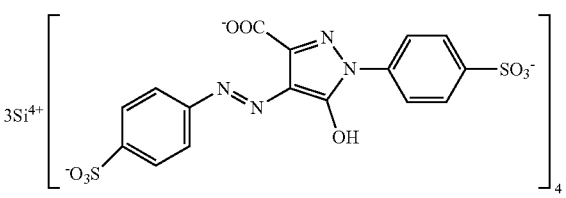

Trisodium (4E)-5-oxo-1-(4-sulfonatophenyl)-4-[(4-sulfonatophenl)hydrazono]-3-pyrazolecarboxylate When Blue Tartrazine reacts with $Cu^{2+}$ in the antimicrobial composition, the following may be formed:

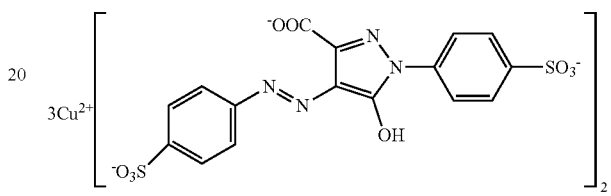

Tri-copper(II) (4E)-5-oxo-1-(4-sulfonatophenyl)-4-[(4-sulfonatophenyl)hydrazono]-3-pyrazolecarboxylate When Blue Tartrazine reacts with $Cu^+$ in the antimicrobial composition, the following may be formed:

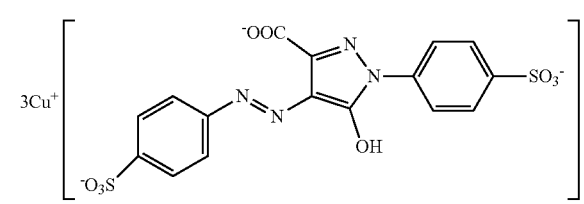

Tri-copper(I) (4E)-5-oxo-1-(4-sulfonatophenyl)-4-[(4-sulfonatophenyl)hydrazono]-3-pyrazolecarboxylate When Blue Tartrazine reacts with $Mn^{2+}$ in the antimicrobial composition, the following may be formed:

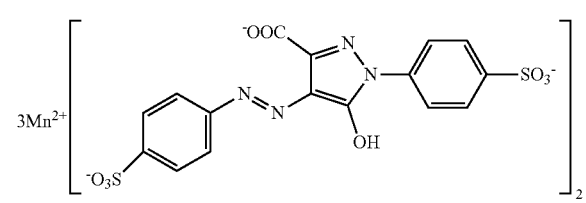

Tri-manganese (4E)-5-oxo-1-(4-sulfonatophenyl)-4-[(4-sulfonatophenyl)hydrazono]-3C-pyrazolecarboxylate When Blue Tartrazine reacts with $Fe^{2+}$ in the antimicrobial composition, the following may be formed:

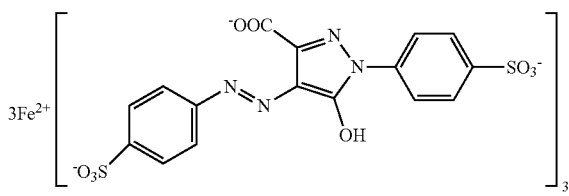

Tri-iron(II) (4E)-5-oxo-1-(4-sulfonatophenyl)-4-[(4-sulfonatophenyl)hydrazono]-3-pyrazolecarboxylate When Blue Tartrazine reacts with $Fe^{3+}$ in the antimicrobial composition, the following may be formed:

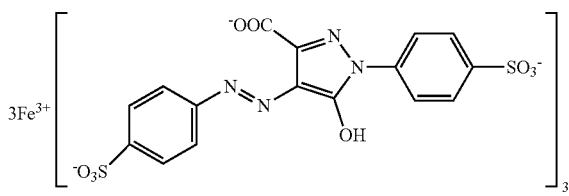

Tri-iron(III) (4E)-5-oxo-1-(4-sulfonatophenyl)-4-[(4-sulfonatophenyl)hydrazono]-3-pyrazolecarboxylate When Blue Tartrazine reacts with $K^+$ in the antimicrobial composition, the following may be formed:

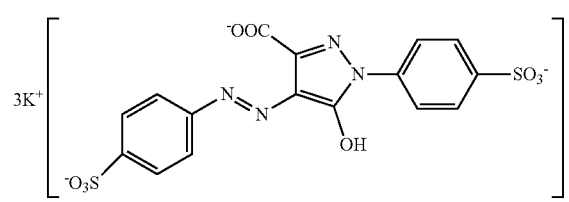

Tri-potassium (4E)-5-oxo-1-(4-sulfonatophenyl)-4-[(4-sulfonatophenyl)hydrazono]-3-pyrazolecarboxylate When Blue Tartrazine reacts with $Al^{3+}$ in the antimicrobial composition, the following may be formed:

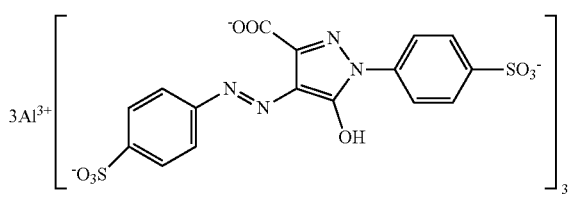

Tri-aluminum (4E)-5-oxo-1-(4-sulfonatophenyl)-4-[(4-sulfonatophenyl)hydrazono]-3-pyrazolecarboxylate When Blue Tartrazine reacts with $Mg^{2+}$ in the antimicrobial composition, the following may be formed:

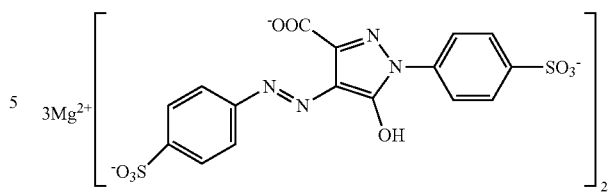

Tri-magnesium (4E)-5-oxo-1-(4-sulfonatophenyl)-4-[(4-sulfonatophenyl)hydrazono]-3-pyrazolecarboxylate When Blue Tartrazine reacts with $Ca^{2+}$ in the antimicrobial composition, the following may be formed:

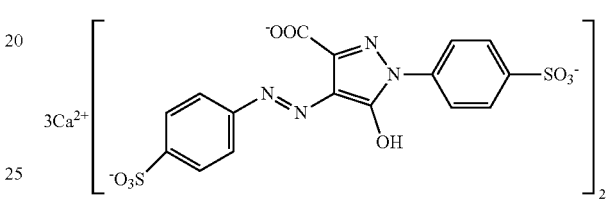

Tri-calcium (4E)-5-oxo-1-(4-sulfonatophenyl)-4-[(4-sulfonatophenyl)hydrazono]-3-pyrazolecarboxylate When Blue Tartrazine reacts with $Zn^{2+}$ in the antimicrobial composition, the following may be formed:

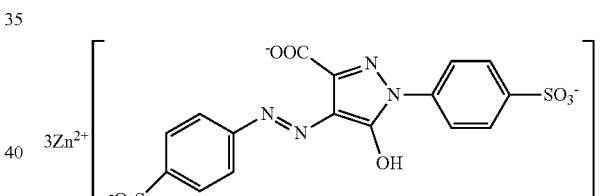

Tri-zinc (4E)-5-oxo-1-(4-sulfonatophenyl)-4-[(4-sulfonatophenyl)hydrazono]-3-pyrazolecarboxylate When Blue Tartrazine reacts with $Ti^{4+}$ in the antimicrobial composition, the following may be formed:

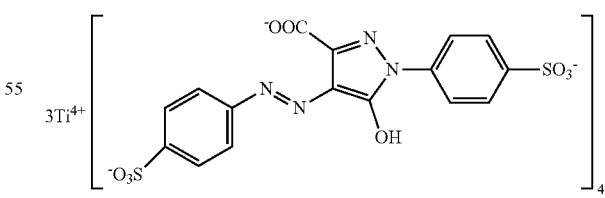

Tri-titanium (4E)-5-oxo-1-(4-sulfonatophenyl)-4-[(4-sulfonatophenyl)hydrazono]-3-pyrazolecarboxylate When Blue Tartrazine reacts with $Mo^{3+}$ in the antimicrobial composition, the following may be formed:

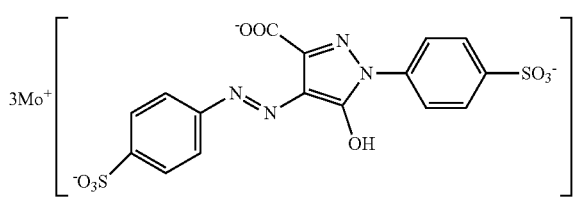

Tri-molybdenum (4E)-5-oxo-1-(4-sulfonatophenyl)-4-[(4-sulfonatophenyl)hydrazono]-3-pyrazolecarboxylate The human body requires essential heavy metals, include Cu, Zn, Mg, and Ca, to carry out biological functions. In the biological system, the metals are mostly bound to proteins. The metalloproteins have both catalytic and structural roles, such as the following: (i) as a constituent of enzyme active sites; (ii) for stabilizing enzyme tertiary or quaternary structure; (iii) for forming weak bonds with substrates, contributing to their orientation to support chemical reactions; and (iv) for stabilizing charged transition sites. Cu, Fe, and Mn have an impaired (or unpaired) electron that allows for their participation in redox reactions, such as those at enzyme active sites.

Mn has unpaired electrons that allow for its participation in redox reactions at enzyme active sites. Cu mediates the reduction of one superoxide anion to hydrogen peroxide and oxidation of a second superoxide anion to molecular oxygen in the active site of cytoplasmic superoxide mutations. Zn has no unpaired electrons in $Zn^{2+}$ and it may prevent the formation of harmful free radicals by competing with the redox active metals, such as Fe and Cu, at the enzyme active sites. The heavy metals may be immediately complexed with molecules or peptides upon entry to the cell.

Biological Function of Lauryl Ether Sulfate and Brilliant Blue:

In the antimicrobial composition of the present disclosure, the presence of sodium laureth sulfate and brilliant blue or blue tartrazine react like a pump membrane and as a barrier between heavy metals and sodium ions by establishing barrier and control the flux of ions in the human body, mainly the sodium ion. This barrier may help fix ions in the human body for wound healing and treating skin infections. It may also react as a regulator of osmosis activity between intra and extracellular by maintaining flux of important elements through damaged cells in skin regeneration and the treatment of skin diseases. It may also rehabilitate mineral elements of the skin in the case of, for example, alopecia treatment. It may also rejuvenate skin and help prevent wrinkles and help the skin remineralize. Lastly, it may penetrate into cells and manage the osmotic pressure for the balance of pressure within cells.

Biological Function of Sodium Chloride or Sodium Ions:

Sodium does not penetrate the cells because of the barrier created by the heavy metal. Thus, the sodium in the composition of the present disclosure does not penetrate the protective membrane. As a result, a net charge is established across the plasma membrane with the interior being negatively charged with respect to the exterior. The accumulation of salt outside of the cells may help maintain osmotic balance of the sodium gradient. The osmotic balance may be fixed by the polystyrene membrane by fixing heavy metal ions into the cells and displacing sodium ions. Finally, sodium ions do not have any biologic function in the wound healing process and skin disease treatment. Rather, the sodium chloride may soften the bond in the composition of the present disclosure. The salt in the cream of the present disclosure may have a cosmetic functions, helping to effectively clean the skin.

Certain molecules and salts included in the composition of the present disclosure may promote the healing of wounds and burns without spots and scars. Those salts include, for example, acidified sodium chloride (NaCl→$Na^+$, $Cl^-$), zinc coceth sulfate, magnesium coceth sulfate, potassium coceth sulfate, calcium coceth sulfate, aluminum coceth sulfate, and aluminum chloride ($Al^{3+}$, $Cl^-$→$AlCl_3$).

Correlation between Silicon and Aluminum:

In the composition of the present disclosure, there may be a correlation between silicon and aluminum reactivity. The correlation demonstrates the link of both elements. Thus, silicon prefers coordination numbers with a tetrahedral atomic environment, while aluminum prefers octahedral coordination in hydrated cations, oxides, hydroxides, and coordination complexes. The isoelectric relationship between $(SiO_2)_2$ and $[AlSiO_4]^-$ may be the foundation of vast aluminosilicate chemistry.

In the case of a clay mineral, this correlation may be:

$$2Al(OH)_3(c)+2H_4SiO_4(aq) \rightarrow Al_2Si_2O_5(OH)_4+5H_2O$$

$$Al_2Si_2O_5(OH)_4+6H^+ \rightarrow 2Al^{3+}+2H_4SiO_4(aq)+H_2O$$

The presence of $Al^{3+}$ may react with $Cl^-$ to create aluminum chloride to stimulate skin regeneration and wound healing.

Potassium Reactivity:

The potassium content in the composition of the present disclosure may be provided by two sources, the water and the kaolin composition. In the kaolin, the $K^+$ ions may be removed by hydrolysis of the kaolin. During its formation, hydrolysis occurs, causing $H^+$ or $OH^-$ to replace ions in the mineral, as explained by the following reaction:

$$4kAlSi_3O_8+4H^++2H_2O \rightarrow 4k^++Al_4Si_4O_{10}(OH)_8+8SiO_2$$

Thus, $K^+$ is removed by dissolution into water. Therefore, in the composition of the present disclosure, the $k^+$ may be activated by processing a mechanical energy in the presence of lauryl ether sulfate and brilliant blue, causing the $K^+$ ion to integrate the interlayer position. Additionally, the mechanical energy may allow the oxygen to react with the composition in the presence of water and lauryl ether sulfate. Thus, the follow complete dissolution may be activated by the mechanical energy:

$$CaCO_3+H_2CO_3 \rightarrow Ca^{2+}+2(HCO_3)^-$$

Wherein $K^+$ is integrated in the interlayer position activated by the mechanical energy during the synthesis process.

Galenic Criteria and Healing Properties of the Cream of the Present Disclosure:

The cream of the present disclosure may heal several diseases including impurities of the skin, burns, wounds, diabetic wounds, leprosy, acne, spots, dead skin, skin blemishes, whitlow, boils, ringworm, stings, and eczema. The cream may also stimulate the minimization of the appearance of fine lines and wrinkles, encourage youthful collagen production, boost the skin's immunity, replenish moisture and soothe excessively dry, lipid-depleted skin. Thus, the cream may act as a medicine and a cosmetic product simultaneously. Explaining the process may require an understanding of the implication of ortho-silicic and organic silicon in the immune system reactivities and the implication of ortho-silicic in correlation with the second law of thermodynamics and entropy.

First, at birth, the immune system is active, which is called innate immunity, but it continues to build and improve during life, which is called acquired immunity. White blood cells limit infections and are usually sufficient to control microbes quickly. For other infections, especially in the case of viruses, other cells (T-cells and plasma cells) take over. These cells intervene the antibodies. The cream of the present disclosure includes organic silica and ortho-silicic acid, which stimulate the immune system, working in strengthening the immune system and regenerating cells with a biological action of laminin and thrombospondin while treating infections. Vitamins, metalloproteins, and trace elements in the cream may provide more precision in the immune action to be more specific and effective for the desired treatment of the skin. Thus, the cream may act like a probiotic skin therapy.

Second, all skin pathology justifies the states of low stability of biochemical reactions in the body. Chemical processes usually occur because they are thermodynamically favorable, meaning from high energy to low energy and from less stable to more stable. Therefore, in the human body, all biochemical reactions tend to be less stable with aging or when people are tired, sleepy, hungry, farting, and sick. Death is a loss of complexity, a loss of organization, and chemical reactions reach a stable level, a great loss of entropy, and disorder. However, the cream, and particularly ortho-silicic acid, challenges thermodynamic stability (skin disease and other pathology), creating physiological entropy to heal skin pathology. Low stability levels of the skin may be due to skin disease, wounds, burns, leprosy, psoriasis, diabetic wounds, skin cancer, and the like. According to galenic criteria, the healing model of the cream is particular in that it acts systematically with specific vitamins or trace elements to induce an immune response, improve cellular communication, and help the human body's immune process against skin disease. The kaolin (or kaolin USP) may be used to control metalloproteins and the specific amounts of trace elements during the synthesis process. Natural kaolin has the same chemical formula and structure as kaolin USP. However, the difference between the two is related to the coloring. Natural kaolin is less white (gray scale) than Kaolin USP, which is due to the purification process to create kaolin USP, which is a washed, white, soft Kaolin with very low levels of trace elements, including low heavy metals. Because of purity levels, the kaolin and kaolin USP do have the same chemical properties, but the organoleptic properties (taste, touch, appearance, and smell) are different.

Galenic Criteria and Implication of the Second Law of Thermodynamics, Entropy, Biological Order, and Disorder of Orth-silicic Acid in the Human Body:

Living systems increase the entropy of their surroundings. Therefore, the cells create ordered structures from less organized starting materials. Simpler molecules are ordered into the more complex structure of an amino acid, and amino acids are ordered into the polypeptide chains. At the organismal level, complex and beautiful orders result from a biological process that uses simpler starting materials. The human body begins to fix silicon from fetal life to the brain, and ortho-silicic acid helps run electricity in the brain. Silicon and ortho-silicic acid is incorporated in large molecules, and silicon is found in the cell, at the heart of its structure (centriole, nucleolus, mitochondria, and cell membrane). Because silicon and ortho-silicic acid are both very abundant in connective tissue, cartilage, skin, and the lymph node, they help to regenerate tissues in wounds by initiating cell growth and regeneration. This means that ortho-silicic acid and silicon challenge thermodynamic level stability and increase the entropy in the human body to create organized and complex structures, leading to the growth and regeneration of cells. The ortho-silicic acid with silicon ($Si^{4+}$) may connect and stabilize free radicals in the human body during cell respiration and other metabolic processes that require oxygen. Also, $Si^{4+}$ may split water and connect with hydroxide ions to form $Si(OH)^{3+}$, $Si(OH)_2^{2+}$, $Si(OH)_3^+$, and $SiO_4^{4-}$.

The silicon and ortho-silicic acid increases entropy and creates ordered cell structures from less organized starting materials. Specifically, the tectosilicate is basically made up of tetrahedral $SiO_4^{4-}$ units linked in their corners by Si—O—Si bonds. The Si—O bond may be under mechanical stress and dissolved.

However, a chemical system is thermodynamically stable when it is at its lowest energy layer. This means any living system is at a most stable level when death occurs. All entities in the universe obey the laws of thermodynamics. The thermodynamic laws govern universe. As for the human and animal, the thermodynamic law may be justified by fatigue, hunger, sleeping, disease, the fart, and sexual impulse specially for the adult, impulse control disorder, aging, and death. In the human body, entropy may be regulated and controlled by the presence of ortho-silicic acid and silicon, which thus may defy or challenge the laws of thermodynamics. Ortho-silicic acid challenges the laws of thermodynamics by promoting the dynamism of body functions that depend on protein. Moreover, ortho-silicic acid challenges the laws of thermodynamics and creates ordered structures by performing cell growth, skin regeneration, establishment of molecular structures, the functioning of metabolism, like the synthesis of collagen, elastin, and hyaluronic acid, the connective tissue, including cartilage, bone, skin, and immunity. In living cells, specifically in humans, the decay in organic silicon with age of the richest tissues (skin, arteries, thymus) is enormous: more than 80% between sexual maturity and the end of life. The level of entropy and thermodynamics are inversely proportional.

The Dynamism of Physiological Entropy in the Human Body:

In a living organ, ortho-silicic acid challenges the laws of thermodynamics and provides good functions of the cell in all metabolic processes, including cell growth, multiplication, and duplication. Thus, ortho-silicic acid may act as an inhibitor or activator in many biochemical mechanisms—structuring and protecting many supporting macromolecules including elastin, collagen, and proteoglycans; acting as a potentiator, causing other molecules to act as therapeutic agents (remedial treatment); detoxifying the body, which promotes membrane depolarization and improves cellular respiration; promoting the mineralization process in ossification; and acting as a structural component and defender of various connective tissues such as bones, cartilage, dermal tissue, and the aorta; functioning in the metabolism of muco-polysaccharides and biopolymers, forming the extracellular substance of many tissues. As a result, silicon may be the body's first therapeutic defense shield. Additionally, taking organic silicon prior to a simultaneous with any other treatment may amplify the effectiveness of the treatment.

Galenic Criteria and Implication of Power of the Antimicrobial Cream

The cream may include natural kaolin or Kaolin USP, wherein Kaolin USP is $(H_2Al_2Si_2O_8H_2O)$ or $Al_2Si_2O_5(OH)_4$ or $Al_2H_4O_9Si_2$. Thus, during synthesis, the following occurs:

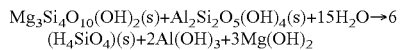
$Mg_3Si_4O_{10}(OH)_2(s)+Al_2Si_2O_5(OH)_4(s)+15H_2O \rightarrow 6(H_4SiO_4)(s)+2Al(OH)_3+3Mg(OH)_2$ The antimicrobial cream may help treat wounds, burns, injuries, leprosy, diabetic wounds with the presence of vitamins A, C, D, and E, and many incurable diseases in the human body and skin. Most incurable diseases result from incorrect cell communication. Sometimes cells send the wrong signals or do not pickup messages correctly. Free radicals are unstable and incomplete oxygen molecules attempt to mate with existing cells to complement each other, wherein this chemical instability may cause the substances to be reaction. Some of the reactions within the cells can lead to damage. Moreover, excess free radicals may have a visible effect on aging skin and may be involved in pathologies such as cancer, heart disease, neurodegenerative diseases, and drug poisoning. A free radical's activity is an important cause of vascular complications in Type 1 diabetes. In this process, ortho-silicic acid with the presence of particular vitamin(s) may be the most active ingredient and provide the physiological entropy for the specific response needed to combat the particular pathology. When a threat occurs, cells communicate rapidly to elicit physiological responses that may help the body handle extraordinary situations. Thus, the ortho-silicic acid in the cream may help cause the physiological response needed to respond to particular situations by connecting and stabilizing any free radicals.

Benefits of the Active Ingredients in the Antimicrobial Cream

Active ingredients include organic silicon or ortho-silicic acid, aluminum hydroxide, and magnesium hydroxide. The silicon or ortho-silicic acid stimulates the immune system and improves cell communication. Aluminum hydroxide helps maintain the pH value at about 7.4. Magnesium hydroxide may interact with sodium chloride or hydrogen chloride and form magnesium chloride, which may act as an antiseptic, stimulate the immune system, activate cell renewal, help fix calcium, detoxify the body, clean the intestines, skin, and the like, promote euphoric and tonic effects, relieve muscle pain, act as a slight laxative, act as a radioprotector, catalyze metabolic reactions, and the like.

Metal and Metalloprotein Sources of the Antimicrobial Cream

In the composition of the present disclosure, the phyllosilicates may be based on a framework of $O_2^-$ and $OH^-$ ions, which may occupy the summits of octahedral assemblies. Cations of various sizes, such as $Si^{4+}$, $Al^{3+}$, $Fe^{3+}$, $Fe^{2+}$, $Mg^{2+}$, $Ti^{4+}$, $Cu^{2+}$, $Cu^+$, $Mn^{2+}$, and $Mo^+$, may be positioned within the elementary structural cavities. This ions are also called metalloproteins, which may have four sources: (1) water; (2) kaolin mineral, (3) talc $(H_2Mg_3(SiO_3))$ or $Mg_3SiO_{10}(OH)_2$; and (4) gelatin. The final product may be $(Al,Zn,Fe^{3+},Fe^{2+},MgO,Mn,Cu^{2+},Cu^+,Ti,Mo^+) Si_4O_{10}(OH)_2 K^+Na^+Ca^{2+}$.

(1) Water: in the composition of the present disclosure, water reactivity may be very important. Water has strong hydrogen bonds, and at room temperature, pure water should be solid. However, the presence of the hydrogen bonds linking the molecules together gives the molecules very particular characteristics and structuring. The structuring is due to the formation of oriented hydrogen bonds, which associate the molecules into tetrahedral structural units and, thus, the liquid differs totally from a stack of molecules that tends to be as dense as possible. The predominant Van der Waals interaction is the interaction of keesom (69%) (dipole-dipole interaction), then the interaction of London (polarization interaction), which is created by the charges induced by the external polarization field. With the presence of lauryl ether sulfate, the molecules subjected to the dipolar interactions may be the predominant interactions in liquid water, and these interactions may be modified in the composition of the present disclosure by the distribution of charges and their way of reacting to the external field. In the clay structure, water molecules modify the cation-clay surface interactions by creating interactions between cation or charged surface and water molecules. This reorganization of the network of interactions existing in the clay structure affects the ability of the clays to hydrate. Water molecules, lauryl ether sulfate, and fatty acids will swell the clay structure and strengthen cation-surface interaction. This implies two things: (1) during hydration, the charges present in the clay structure change as the amount of water increases, and (2) the variation in partial loads depends on the compensating cation and its hydration energy. The modifications of the loads may allow the clay to absorb more water, facilitating the spacing of the antimicrobial cream's layers. This dynamic aspect of the electrical interactions may help the composition create the biological environment to process the remineralization of the skin and healing wounds by the hydration of clays, which may be the cause of the swelling of mineral clays. In the vicinity of the interface with clay, the water may have its structure modified by interactions by the surface.

The water's composition may include calcium ions 112 mg/L; magnesium ions 12.5 mg/L; silicon dioxide 7.1 mg/L; potassium ions 2.5 mg/L; sodium ions 10 mg/L; zinc ions 3.5 mg/L; copper 1.1 mg/L; iron 0.3 mg/L; and manganese ions 0.05 mg/L.

(2) Kaolin mineral (clay mineral composition): in the composition, the clay mineral may absorb certain ions and retain them in an exchangeable state, wherein exchangeable ions are held on the external surface of the mineral, and the exchangeable ions do not affect the structure. The following list presents the most exchangeable cations in order of usual relative abundance: $Ca^{2+}$, $Mg^{2+}$, $H^+$, $Na^+$, $Fe^{3+}$, $Fe^{2+}$, $Ti^{4+}$, $Cu^2$, $Cu^+$, $Mn^{2+}$, and $Mo^+$.

The clay (kaolin) composition may have a pH of about 7.3 and may comprise the following: $SiO_2$ (48.10%); $Al_2O_3$ (36.85%); $Fe_2O_3$ (0.05%); $TiO_2$ (0.52%), $CaO$ (0.28%); and $K_2O$ (0.36%), wherein all percentages are mass percentages.

(3) Talc $(H_2Mg_3(SiO_3))$ or $Mg_3SiO_{10}(OH)_2$): talc is a hydrous magnesium silicate mineral. Although the composition of talc usually stays close to the above generalized formula, some substitution does occur. Small amounts of Al or Ti can be substituted for Si; small amounts of Fe, Mn, and Al can be substituted for Mg; and very small amounts of Ca can be substituted for Mg. When large amounts of Fe substitute for Mg, the mineral is known as minnesotaite. When large amounts of Al is substituted for Mg, the mineral is known as pyrophyllite.

The talc composition may include the following: magnesium (19.23% Mg and 31.88% MgO); silicon (29.62% Si and 63.37% $SiO_2$); hydrogen (0.53% H and 4.75% $H_2O$); and oxygen (50.62% O), wherein all percentages are mass percentages.

(4) Gelatin: as a denatures product of collagen, gelatin contains may divalent metal ions, such as calcium, copper, and zinc that can form ionic bonds with carboxylic acid and groups on the gelatin polypeptides, influencing the organization for the gelatin network. However, there is little information on the impact of divalent ions on the stability and mechanical properties of gelatin hydrogels. Removal of the metal ions may free the carboxylic acid group in polypeptide molecules, thereby strengthening the electrostatic interactions between the carboxylic acid groups and also improving the crosslinking density upon chemical crosslinking, eventually improving the mechanical strength and stability in the antimicrobial composition. The gelatin may provide stability, strengthen the link by influencing the electrostatic relations between lauryl ether sulfate, Brilliant Blue, metalloproteins, and the tetrahedral and octahedral relationships of aluminum (gibbsite) and silicate ($SiO_2$).

Cation Exchange Acceleration:

there may be two major reasons for cation exchange acceleration in the composition of the present disclosure. (1) The amount of sodium chloride and the polystyrene sulfonate (Brilliant Blue and lauryl ether sulfate) may accelerate the exchange because of polystyrene sulfonate's properties. They may each also act as a softening agent due to Van der Waals forces between the top silica layers. (2) The broken bonds around the crystal edge and the substitution within the lattice and the hydroxyl hydrogen surface may be exchangeable, because the $OH^-$ concentration increases the negative charges at the edges according to, for example, the following: $SiOH+OH^- \rightarrow SiO^-+H_2O$. The same applies to Al—OH at the exposed base surface.

Properties and Characteristics

The green tea in the cream of the present disclosure may help fight inflammation. Moreover, the green tea has antioxidant properties and may enhance the wound healing process. The salt may have strong cleansing properties. The talc may be a mineral comprising Mg, Mn, Ti, Fe, and Ca, such as hydrated magnesium silicate ($H_2Mg_3(SiO_3)$ or $Mg_3SiO_{10}(OH)_2$. The menthol ($C_{10}H_{19}OH$) may relieve minor aches and pains. Clove oil may be used for its antiseptic properties. Additionally, it contains eugenol, which has anti-bacterial properties; thus, the clove oil may help clear cystic acne and kill infections, thus reducing swelling. Olive oil may help fight signs of aging. The honey used in the cream of the present disclosure may be a saturated or super saturated solution of sugars. The honey may be diluted by wound exudates, creating hydrogen peroxide via a glucose oxidase enzyme reaction and resulting in antibacterial activity that does not damage the tissue.

The vitamins included in the cream may have various purposes. For example, vitamin A may help rebuild tissue by playing a role in the development of lymphocytes, which are cells that fight off bacteria and disease. Vitamin D may contain effective antioxidants that help fight free radicals in the body. Vitamin C may provide potent antioxidant protection, healing the skin from damage from free radicals, may boost healthy collagen production, may reduce the appearance of brown spots and other sun damage, may reduce inflammation and irritation, may fade post-breakout red marks, and may increase the effectiveness of sunscreens. Vitamins B2 may promote metabolism and mobilize iron from storage to incorporate into cells. Vitamin B6 may help utilize the energy contained in food and is important for carbohydrate, protein, and fat metabolism.

The cream of the present disclosure may have a clay-like consistency, wherein the ingredients of the cream may stimulate the regeneration of skin cells. Thus, facials masks and exfoliating scrubs made with the cream may result in the stem cells located within the skin actively generate differentiating cells that may ultimately form either the body surface or the hairs that emanate from it. The stem cells may be able to replenish themselves, continually rejuvenating the skin and hair.

Plasticity and Breaking Point:

In the antimicrobial cream of the present disclosure, the mechanical properties, such as plasticity and breaking point, may be influenced by the nature and quantity of the absorptive ions, in particular the $Ca^{2+}$ or $Na^+$ ions. The addition of an additional quantity of sodium chloride during the synthesis process may activate the exchange capacity between the clay and the polystyrene sulfonate, namely the Brilliant Blue and the lauryl ether sulfate. However, the ionic strength may not have a considerable effect, so there may be an effect of the loss of surfactant by the precipitation due to the exchange of salts. The absorptions of the anionic surfactant, lauryl ether sulfate, may increase as the concentration of electrolytes or cations increase. The colloids may be provided with negative charge.

Mixed layer clays may comprise a clay that changes from one type to another through a stacking sequence. The cream of the present disclosure is layered in the following order mineralized water (Mg, Na, Ca, Fe, Zn, Mn, K, etc.), fatty acids, lauryl ether sulfate, talc ($Mg_3SiO_{10}(OH)_2$), and mineral kaolin clay contents (60% silica, 26% aluminum, and 14% Mg, Fe, Na, K, Ca, Mo, Ti, $H_2O$), wherein all percentages are mass percentages.

During the synthesis process, the main agent responsible for the chemical reaction together with mechanical energy is water. Because of the presence of $(Ca, Na, H)(Al,Mg,Fe,Zn)_2(si,Al)(O)*H_2O$ and because the most common weak acid that forms in surface water is carbonic acid, the result is $H_2O+CO_2 \rightarrow H_2CO_3+H^++HCO_3$, wherein the $H^+$ is a small ion that can enter the crystalline structure easily and release another ion. Therefore, with the presence of Brilliant Blue and lauryl ether sulfate together with mechanical energy, the following is formed: $(Al,Zn,Fe,67MgO_{33})Si_4O_{10}(OH)_2Na^+Ca^{2+}$.

Potential Energy and Stereochemistry:

The potential energy provided by the chemical reactions may spin compound movements and provide an extraordinary healing power.

Mutation or Isomorphism and Polymorphism Substitution Structure of Antimicrobial Cream:

The swelling properties of the cream of the present disclosure may be due to the positive interlayer in excess with some OH. The metal oxide and metal may perform isomorphism substitution, wherein they relocate in octahedral and tetrahedral layers. During the synthesis process, there may be two basic components to the structure of a layer of corner linked tetrahedral and a layer of edge sharing octahedral. Because the dominant ions in the cream are $Al^{3+}$ and $Si^{4+}$, they relocate and substitute and produce the deficiency charge that must be balanced. Consequently, isomorphism substitution occurs. Moreover, during the synthesis process, which requires mechanical energy, such as cracking and mixing of kaolin with water, fatty acids, lauryl ether sulfate, and talc, there is about 60 to about 65% by mass silicon. The silicon may be present as montmorillonite (Si—Al—Si) or kaolinite (Al—Si—Al). Magnesium may also be present as montmorillonite (Al—Mg—Al). The alternating $Al^{3+}$ and $Si^{4+}$ layers create a polymorphism substitution, changing the structure and disrupting the crystallinity through kaolinite, chlorite, and montmorillonite. This generally occurs when a chemical compound may crystallize in more than one structure. This change creates the deficiency in charge that needs to be balanced. Thus, the swelling of the composition is caused by two things (1) the isomorphism substitution with compensatory cation imbalance; and (2) the polymorphism substitution activated by the addition of talc, cracking the phyllosilicate clay and polystyrene sulfonate.

The dominant atom in the tetrahedron is the $Si^{4+}$ cation, but the $Al^{3+}$ cation can also be positioned at this site. However, the substitution of the $Al^{3+}$ for $Si^{4+}$ produces a charge deficiency that must be balanced.

The octahedral layers are edge sharing octahedral layers. The phyllosilicate have hydroxyl ($OH^-$) ions involved in the linkage to form layers, in addition to the oxygen.

During the synthesis, the composition of the present disclosure starts with a kaolinite structure with an alternating structure of alumina and silica layers. Once talc is added, the structure changes to montmorillonite with very weak silicate-silicate bonds softened by water, cations ($Ca^{2+}$, $Mg^{2+}$, $H^+$, $Na^+$, $Fe^{3+}$, $Fe^{2+}$, $Ti^{4+}$, $Cu^{2+}$, $Cu^+$, $Mn^{2+}$, and $Mo^+$), lauryl ether sulfate, and fatty acid. The change in structure is due to the large amount of silicon (67% by mass) provided by the talc and kaolinite mineral in the octahedral site, wherein the mixture may also be activated using mechanical energy, which allows some oxygen or $OH^-$ bonds between aluminum and silicon to be broken. There is also the presence of aluminum-silicon bonds and magnesium in the octahedral sites. Due to the structure, the clay may absorb the water between its layers.

Because of the thin layers, the clay gives the water an enormous surface on which chemical reactions may also take place, wherein elements such as potassium, sodium, or calcium may bind to the clay and be given back to the water, each time in exchange with another element from that group. Thus, it may be said that the clay has the ability of "cation exchangers." During this exchange, the macroscopic characteristics of the clay may also change permanently, wherein the clay becomes rough or more plastic and swells. This change may be due to the mixture of kaolin and talc mineral together with the mechanical energy activation. Thus, the presence of talc may cause the change of structure activated by mechanical energy, water, lauryl ether sulfate, and fatty acid.

The composition of the present disclosure is mainly a montmorillonite structure and some kaolinite and chlorite structure. Specifically, each silicate crystal includes a quasi-regular tetrahedral (($Si,Al)O_4$) whose centers are occupied by silicon or aluminum ions, and the vertices have oxygen ions. The $Si^{4+}$ ion has a radius of 0.039 nm with a coordination number of 4, meaning that it is surrounded by four oxygen atoms, forming a quasi-regular $SiO_4$ tetrahedron. Each of the oxygens is attracted by the central silicon with a stronger binding strength than those of the other cations with which it is also in contact. The aluminum has a radius of 0.057 nm and a coordination number that varies from 4 to 6. The aluminum can thus create $AlO_4$ tetrahedra or $AlO_6$ octahedrons. The tetrahedral $(Si, Al)O_4$ may be independent or may associate by their vertices, but such tetrahedral may not have an edge or face in common. This arrangement of tetrahedral $(Si, Al)O_4$ has a negative charge that neutralizes the cations. The cations, such as hexagonal Mg, Fe, and Al, are found at the centers of the quasi-regular octahedrons of oxygen atoms, the edges of which have a length close to that of the tetrahedron $SiO_4$. Thus, the silicates that have a geochemical significance appear as arrangements of oxygen tetrahedral and octahedral with common edges. The silicates themselves have quasi-regular tetrahedral of the oxygen ions with their centers either including a silicon or aluminum ion, associated by the four vertices to form a three-dimensional framework of $(Si, Al)O_2$ constituting a macroanion whose negative charge is neutralized by certain cations. Because the aluminum atom plays the geometric role of the silicon atom, the silicates appear as aluminosilicates, in which the Si atoms are at least as numerous as the Al atoms. Thus, an oxygen ion may be bonded to two other ions, which makes it inactive or with two ions, $Si^{4+}$ and $Al^{3+}$, giving it an electrostatic valent of 1+¾. This active oxygen is therefore bound to cations from which it receives ¼ of electrostatic valence to neutralize its charge.

Ions, such as $Mg^{2+}$ and $Fe^{2+}$ with a coordination number of 6 at the regular octahedron centers of oxygen atoms have an electrostatic valence of ⅓, which is too large compared to other cations attached to the negative colloids to create an electrostatic bond. Thus, they never enter the chemical composition of silicates. On the other hand, larger ions, such as $Ca^{2+}$ and $Ba^{2+}$ with a coordination number of 8, or alkaline ions $K^+$, $Na^+$, and $Li^+$, whose electrostatic valence remains less than ¼, are suitable. However, in some silicates, small amounts of iron are present in the form of $Fe^{3+}$, which replace $Al^{3+}$ in the oxygen tetrahedral.

In the antimicrobial cream of the present disclosure, the elementary layer may be an octahedral or tetrahedral layer. To form a polymer cream, the octahedral and tetrahedral layers may alternate tetrahedral layers including an octahedral layer, which may cause the isomorphism substitution, polymorphism substitution, and swelling in the cream, which is hydrophilic. The elementary layer bay be succeeded by a complete layer of brucite type $Mg(OH)_2$, in which a part of $Mg^{2+}$ is replaced by $Al^{3+}$. Additionally, in the crystalline forms of the antimicrobial composition, every four points (oxygen atoms) of the $SiO_4$ structure are shared with other tetrahedrals via Van der Waal bonds. The resulting relative amounts of silicon and oxygen in the crystal structure result in the net chemical formula $SiO_2$.

Along with the Van der Waal bonds between the top silicate tetrahedral position, there may also be hydrogen bonds between inorganic colloids, cations, and silicon. This hydrogen bond may influence the silicate to react with the colloid and attach a metal by a weak bond. Because of the structure of the quasi-regular $SiO_4$ tetrahedron wherein the oxygens are attracted to the central silicon with a stronger binding strength than those of other cations, the crystalline structure results in the chemical formula $SiO_2$. Thus, some hydrous metal silicate compounds may be established, and the silicate structure may by hydrous sodium silicate, hydrous potassium silicate, or lithium silicate. These compounds may influence the arrangement of silicate in the composition. These arrangements may be present due to the addition of talc with the kaolin clay mineral and the cracking process during synthesis. Specifically, in the cream of the present disclosure, silicon may be present in certain parts of the cream as follows.

First, silicon may be present in independent silicates, wherein no oxygen atom is bonded to two silicon atoms. The $SiO_4$ tetrahedral anions are associated with cations like $Mg_2SiO_4$, where a hydrogen bond is present between ions and a Van der Waals bond is present at the top of each silicate.

Second, silicon may be present in silicates with finite tetrahedral groups, wherein the tetrahedral of the same group may be combined in the minerals such that an oxygen atom is a common sum with two $Si_2O_7$. Thus, there may be a hydrogen bond between a cation and inorganic colloid and a Van der Waals bond at the top of each silicate, wherein the top of the silicate is defined as the interlayer connection by Van der Waals attractions.

Third, the silicon may be present in silicates arranged in chains, wherein the tetrahedrals combine to form an infinite linear chain, and the corresponding silicates may have a fibrous texture. When the chain is a simple chain, its chemical composition is $SiO_3$, and the properties are similar to the tetrahedral anion $SiO_2(OH)$. This arrangement may include hydrous sodium silicate with a hydrogen bond between colloids and a Van der Waals bond at the top of each silicate.

Fourth, the silicon may be present in a lamellar silicate, wherein the tetrahedron chains pool some of the vertices to form planar networks. Thus, two chains of juxtaposed pyroxenes, of link $SiO_3$, provide the double chain of the amphiboles $Si_4O_{11}$. If the chain continues so that three atoms of each of the tetrahedral are common to three other tetrahedral, a planar array of tetrahedrons bound by three of their vertices whose chemical composition is $Si_2O_5$ is formed.

All of the above structural type of silicates may be rotated and organized during the synthesis process of the cream of the present disclosure due to the swelling process caused by the cation imbalance created with the presence of Brilliant Blue, fatty acids, and lauryl ether sulfate. The structures and ions present in the cream composition provide the cream with properties and qualities that result in extraordinary healing powers. In the presence of gelatin, vitamins, polystyrene sulfonate, and fatty acids, the cream of the present disclosure may have the final chemical formula of:

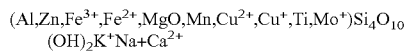

$(Al,Zn,Fe^{3+},Fe^{2+},MgO,Mn,Cu^{2+},Cu^+,Ti,Mo^+)Si_4O_{10}(OH)_2K^+Na+Ca^{2+}$

The cream of the present disclosure may help skin respond to two major threats: the loss of blood and the loss of a physical barrier (the epidermis) between patient innards and the outer world. An open cut is an open doorway to bacteria and other pathogens, far more vulnerable to infection. As a result of certain molecules and salts, the cream of the present disclosure may help promote the wound healing process without spots and scarring. Specifically, the antimicrobial cream of the present disclosure may have the strong ability to help promote blood clotting and stop bleeding, which may be useful in first aid and other treatments. Examples of those molecules and sales include acidified sodium chloride, zinc coceth sulfate, magnesium cocet sulfate, silicon, zinc oxide, titanium oxide, titanium coceth sulfate, calcium coceth sulfate, copper coceth sulfate, iron (iii) and iron (ii) coceth sulfate, aluminum coceth sulfate, manganese coceth sulfate, and molybdenum coceth sulfate.

The addition of NaCl to the cream of the present disclosure may accelerate the cation exchange between negative colloids, water, clay, Brilliant Blue, and lauryl ether sulfate. The NaCl stabilizes the pH of the cream of the present disclosure. During the synthesis process, the addition of NaCl may accelerate the cation exchange between negative inorganic colloids and cations container in the water, such as mineral cations provided by talc and kaolin and/or cations provided by lauryl ether sulfate and blue tartrazine. Moreover, the sodium softens the bond in the interlayer, octahedral, and tetrahedral sites. Additionally, the NaCl forms oppositely charged ions that are held together by an ionic bond, forming a crystal lattice. Ionic compounds (KCl, $AlCl_3$, $CaCO_3$, $MgCl_2$, $FeCl_3$, and $Al(OH)_3$) are formed. The reactions are summarized below.

$Al(OH)_3 + 3Na^+(aq) + 3Cl^-(aq) \rightarrow AlCl_3(s) + 3Na^+(aq) + 3OH^-(aq)$ $Fe(OH)_3 + 3Na^+(aq) + 3Cl^-(aq) \rightarrow FeCl_3(s) + 3Na^+(aq) + 3OH^-(aq)$ $Mg(OH)_2 + 3Na^+(aq) + 3Cl^-(aq) \rightarrow MgCl_2(s) + 2Na^+(aq) + 2OH^-(aq)$ $H_3O^+(aq) + OH^-(aq) \leftrightarrow H_2O(l)$ pH=7.4

Function of Calcium Carbonate Hydrolysis in the Antimicrobial Cream: In the cream of the present disclosure, the buffer system ($H_2CO_3/HCO_3^-$) stabilizes the pH to 7.4. With the presence of water, the following occurs:

$H_2O + CO_2 \leftrightarrow H_2CO_3 + H^+ + HCO_3^-$ $CaCO_3 + H_2CO_3 \leftrightarrow Ca^{2+} + 2(HCO_3^-)$ $H^+ + HCO_3^- \leftrightarrow H^+ + CO_3^{2-}$ pH=7.4

The buffer system is an $H_2CO_3/HCO_3^-$ buffer system in the antimicrobial cream, which keeps the cream at the proper pH.

Types of Bonds in the Antimicrobial Cream:

Several types of bonds are present in the antimicrobial cream of the present disclosure (1) Pauling bond in $SiO_4$; (2) ionic bonds; (3) hydrogen bonds; (4) Van der Waals bonds; (5) attractions between permanent dipoles and dipoles in induced nonpolar molecules; and (6) attractions between nonpolar molecules.

In some embodiments, the cream may be synthesized using a 3-phase process: (1) creating an anti-microbial colloid liquid, which may be blue; (2) creating an anti-microbial solid, which may be green; and (3) creating an anti-microbial, creamy, gelatinous solid and vitamin, which may be green. Mixing of the cream may be done with a mixer coated with a plastic material. This specific type of mixer may be needed because the skin cream is rich in mineral elements, trace elements, weak acids, and vitamins. Examples of each step are described below.

Example 1: Creating the Anti-Microbial Colloid Liquid 2.2 kg of salt were mixed in a phase manner with water. Sodium lauryl ether sulfate and 0.6 oz (or 18 g) of blue tartrazine were mixed in with the salt water, creating the anti-microbial colloidal solution having a blue color.

Example 2: Creating the Anti-Microbial Solid

The colloidal blue anti-microbial solution prepared in Example 1 was mixed with 25 L olive oil; 25 L clove oil; 20 L honey; 5 L green tea; 10 L aloe vera; a 260 kg mixture comprising kaolin gray, phyllosilicates, and aluminum silicate hydrates; 20 kg of talc; and 20 L of mineral oil. The solution was mixed thoroughly using a plastic coated blender, resulting in a green clay cream. It could have alternatively been mixed using just a plastic mixing spoon.

Example 3: Creating the Anti-Microbial, Creamy, Gelatinous Solid 95 kg of gelatin was slightly warmed to about 40° C. with 100 g of menthol to create a diluted solution. The amount of gelatin may be changed to change the viscosity of the skin cream. In embodiments, the gelatin may be added as a granular powder, which would swell when stirred into water. When dry gelatin is used, it may be used in an amount such that a water/gelatin mixture would not exceed about 34% gelatin. While warming, the gelatin solution may be allowed to hydrate for about 30 min. The diluted solution was poured into a mixing bowl. The green clay cream from Example 2 was then mixed into the mixing bowl. While the composition is being blended, it was simultaneously cooled to about 37° C. After cooling, vitamins are added to the mixture, which is then mixed again, creating antimicrobial green cream Kaolin clay, gelatinous and bright (the cream of the present disclosure).

The resulting cream includes silica, aluminum, calcium, and potassium as major elements and copper, lithium, molybdenum, and cobalt as minor elements. Some embodiments of the cream have a formula represented by $(Al,Zn, Fe_1,67MgO_{33})Si_4O_{10}(OH)_2Na^+Ca^{2+}$ plus weak acids, such as benzoic acid, fatty acids, such as ascorbic acid, vitamins, and an antimicrobial agent. The mineral content of the product may vary due to the impurities.

The cream has anti-microbial and antibiotic properties and comprises trace elements, minerals, protein, polypeptides, and a weak acid, such as benzoic acid, which may give the cream its anti-aging and anti-microbial properties.

To use the cream of the present disclosure, a user may apply it externally on the skin or internally. When the cream is applied to the skin, transduction may occur, causing physical energy to be converted into energy used by the nervous system and reducing tension and anxiety in a user. For large wounds and burns, the cream may be gently rubbed on the wound or burn and covered with a compress when dry. The pain may be inhibited and the wound may heal without forming a scar. The cream may be removed from the body after the wound is healed by hydrotherapy, which may eliminate toxins.

The cream of the present disclosure may clean the skin of all or substantially all impurities, such as acne, spots, dead, skin fat, and the like. The cream may also have the ability to clean the face, heal most skin blemishes, whitlow, boils, ringworm, burns, stings, lesions, and the like. The cream may also be able to curb the proliferation of parasites, harmful bacteria, and microbes. The cream may also drain impurities, such as puss, from fabric, as the cream absorbs excess liquid and neutralizes the actions of various alkaloids. Moreover, the cream may have the ability to clean the blood and lymphatic system. The cream may also reinforce defenses, revitalize organs, neutralize poisons, strengthen bones, and reduce inflammation. In some embodiments, the cream may be used to nourish the scalp in cases of alopecia. Furthermore, the cream may help reduce or heal common hemorrhoid symptoms, including painless bright red blood from the rectum, anal itching, anal pain, tender lumps near the anus. Specifically, the cream of the present disclosure may have the ability to heal hemorrhoids in a maximum of about 3 or 4 days, wherein this may be possible due to the presence of coceth zinc sulfate, ZnO, and $TiO_2$. The cream may also have a strong ability to help with blood clotting and stopping bleeding, which may be useful in first aid, treatment, disinfection, and amputations.

Due to its composition, the cream of the present disclosure may ensure the use of physicochemical means of combating the presence and proliferation of microorganisms. Moreover, the cream has bactericidal, virucidal, fungicidal, and sporicidal properties due to its composition and ingredients.

While the composition of the present disclosure is described above in cream-form, it may also be presented in other forms, such as a dietary or injectable form. The dietary form may provide an efficient medicine to cure, improve, or prevent many diseases, such as stress, depression, anxiety, insomnia, and the like with the presence of magnesium chloride. It may also cure gastric ulcers with the presence of aluminum hydroxide. The presence of ortho-silicic acid or organic silicon may stimulate the immune system and improve cell communication, among other benefits described above.

The injectable form may be used with a soluble absorbable organic silicon compound. For example, it may include 0.01 mL silicon solution (silanol) and 0.01 mL saline solution. Because aluminum hydroxide may be used as a vaccine adjuvant, the injectable form may also be effective.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A cream for the skin, the cream comprising:
   gray clay kaolin;
   sodium lauryl ether sulfate;
   blue tartrazine;
   a member selected from the group of organic silicon and ortho-silicic acid;
   sodium chloride;
   menthol;
   metabisulfite sodium;
   gelatin;
   mineral oil;
   olive oil;
   oil of cloves;
   water;
   green tea;
   talc;
   honey; and
   aloe vera,
   wherein the cream comprises:
      about 55 to about 65% by mass silicon;
      about 7 to about 27% by mass aluminum;
      about 10 to about 22% by mass iron; and
      about 25% by mass of other oxides.

2. The cream of claim 1, further comprising perfume.

3. The cream of claim 1, further comprising a mixture of vitamins.

4. The cream of claim 3, wherein the mixture of vitamins comprises vitamin E, vitamin D, vitamin C, vitamin B2, vitamin B5, vitamin H, and vitamin B6.

5. The cream of claim 1, further comprising apple perfume, vitamin E, vitamin C, vitamin B2, vitamin B5, vitamin H, vitamin B6, and vitamin D.

6. The cream of claim 5, wherein a batch of the cream comprises:
   about 260 kg gray kaolin clay;
   about 4 kg sodium lauryl ether sulfate;
   about 0.6 oz blue tartrazine;
   about 2.2 kg sodium chloride;
   about 100 g menthol;
   about 50 g metabisulfite sodium;
   about 95 kg gelatin;
   about 20 L mineral oil;
   about 25 L olive oil;
   about 25 L oil of cloves;
   about 20 L water;
   about 20 kg talc;
   about 5 L green tea;
   about ⅛ L perfume;
   about 5 L honey;
   about 10 L aloe vera;
   about 2,000 international units (IU) vitamin E;

about 100,000 IU vitamin A;
about 300 mg vitamin C;
about 100 mg vitamin B2;
about 250 mg vitamin B5;
about 2.5 mg vitamin H;
about 100 mg vitamin B6; and
about 400 IU vitamin D.

7. The cream of claim 1, wherein the cream comprises about 60% gray clay kaolin.

8. The cream of claim 1, wherein the cream has a pH of about 7.4.

9. The cream of claim 1, wherein a molecular structure of the cream includes an octahedral layer, an interlayer, and a tetrahedral layer.

10. The cream of claim 1, wherein the cream comprises:
   silica, aluminum, calcium, and potassium as major elements; and
   copper, lithium, molybdenum, and cobalt as minor elements.

* * * * *